US009063393B2

(12) United States Patent
Kimoto et al.

(10) Patent No.: US 9,063,393 B2
(45) Date of Patent: Jun. 23, 2015

(54) IN-VIVO IMAGE CAPTURING SYSTEM

(75) Inventors: Seiichiro Kimoto, Hachioji (JP);
Toshimasa Akagi, Hachioji (JP)

(73) Assignee: OLYMPUS MEDICAL SYSTEMS CORP., Tokyo (JP)

(*) Notice: Subject to any disclaimer, the term of this patent is extended or adjusted under 35 U.S.C. 154(b) by 2409 days.

(21) Appl. No.: 11/642,234

(22) Filed: Dec. 20, 2006

(65) Prior Publication Data
US 2008/0015411 A1 Jan. 17, 2008

(30) Foreign Application Priority Data

Dec. 20, 2005 (JP) .................................. 2005-366741

(51) Int. Cl.
| A61B 1/04 | (2006.01) |
| A61B 1/00 | (2006.01) |
| G03B 19/02 | (2006.01) |
| A61B 1/045 | (2006.01) |
| A61B 5/07 | (2006.01) |
| G03B 19/22 | (2006.01) |
| A61B 5/06 | (2006.01) |

(52) U.S. Cl.
CPC .............. *G03B 19/023* (2013.01); *A61B 1/041* (2013.01); *A61B 1/045* (2013.01); *A61B 5/073* (2013.01); *A61B 2562/0219* (2013.01); *G03B 19/22* (2013.01); *A61B 1/00009* (2013.01); *A61B 1/00055* (2013.01); *A61B 1/00156* (2013.01); *A61B 1/00181* (2013.01); *A61B 5/067* (2013.01)

(58) Field of Classification Search
USPC ................................. 600/109, 117, 118, 160
See application file for complete search history.

(56) References Cited

U.S. PATENT DOCUMENTS

| 6,904,308 | B2 | 6/2005 | Frisch et al. | |
| 7,295,226 | B1* | 11/2007 | Meron et al. | 348/77 |
| 2002/0042562 | A1* | 4/2002 | Meron et al. | 600/361 |
| 2002/0198439 | A1 | 12/2002 | Mizuno | |
| 2003/0020810 | A1* | 1/2003 | Takizawa et al. | 348/68 |
| 2003/0023150 | A1 | 1/2003 | Yokoi et al. | |
| 2003/0073935 | A1* | 4/2003 | Segawa et al. | 600/593 |
| 2004/0176685 | A1* | 9/2004 | Takizawa et al. | 600/424 |
| 2004/0199061 | A1 | 10/2004 | Glukhovsky | |

(Continued)

FOREIGN PATENT DOCUMENTS

| JP | 06-114064 | 4/1994 |
| JP | 2003-19111 | 1/2003 |

(Continued)

OTHER PUBLICATIONS

Japanese Office Action Dated Aug. 9, 2011 together with English translation.

(Continued)

*Primary Examiner* — Thomas J Sweet
*Assistant Examiner* — Alexandra Newton
(74) *Attorney, Agent, or Firm* — Scully, Scott, Murphy & Presser, PC

(57) ABSTRACT

Provided is an in-vivo image capturing system including a capsule casing, an analyzing unit, and a warning unit. The capsule casing is insertable into a body of a subject from an oral cavity and it includes an imaging optical system which may obtain images only in one end direction. The analyzing unit analyzes the image components within the oral cavity obtained by the imaging optical system. The warning unit issues a warning to a user about the direction of the capsule casing based on the analytical result by the analyzing unit.

10 Claims, 19 Drawing Sheets

(56) References Cited

U.S. PATENT DOCUMENTS

| | | |
|---|---|---|
| 2005/0004474 A1 | 1/2005 | Iddan |
| 2005/0107666 A1 | 5/2005 | Glukhovsky et al. |
| 2005/0196023 A1 | 9/2005 | Chen et al. |

FOREIGN PATENT DOCUMENTS

| | | |
|---|---|---|
| JP | 2003-70728 | 3/2003 |
| JP | 2003-116781 | 4/2003 |
| JP | 2003-526413 A | 9/2003 |
| JP | 2004-129949 A | 4/2004 |
| JP | 2004-344655 A | 12/2004 |
| JP | 2005-013338 A | 1/2005 |
| JP | 2005-503182 A | 2/2005 |
| JP | 2005-278817 | 10/2005 |
| JP | 2005-304595 | 11/2005 |
| WO | 01/50941 A2 | 7/2001 |
| WO | 02/054932 A2 | 7/2002 |
| WO | WO 2004/082472 A1 | 9/2004 |

OTHER PUBLICATIONS

European Search Report dated Feb. 8, 2013 from corresponding European Patent Application No. EP 06 84 2905.9.

* cited by examiner

IN-VIVO IMAGE CAPTURING SYSTEM

CROSS-REFERENCE TO RELATED APPLICATIONS

This application is based upon and claims the benefit of priority from Japanese Patent Application No. 2005-366741, filed Dec. 20, 2005, the entire contents of which are incorporated herein by reference.

BACKGROUND OF THE INVENTION

1. Field of the Invention

The invention relates to an in-vivo image capturing system such as a capsule endoscope which is inserted into a body of a subject in order to obtain images of inside the subject.

2. Description of the Related Art

In recent years, swallowable capsule endoscopes are developed in the field of endoscopes. Provided with an imaging function and a radio function, the capsule endoscope passes through the internal organs such as esophagus, stomach, and a small intestine with peristaltic motion and obtains images sequentially from the time when a patient swallows it from the mouth for observation of the body cavity until it is naturally discharged from the body.

For example, according to Japanese Patent Application Laid-Open No. 2003-19111, while the capsule endoscope is moving inside the body cavity, image data obtained within the body by the capsule endoscope is sequentially transmitted to the outside of the body through radio communication and stored in a memory set in a receiving device outside the body. A doctor or a registered nurse may make a diagnosis based on the images displayed on a display according to the image data stored in the memory.

In this kind of capsule endoscope, a monocular capsule endoscope is generally used, in which an imaging device such as a CCD is mounted only on one side and it may obtain images only in one direction (one end direction). The monocular capsule endoscope, however, is difficult to determine an imaging direction thereof because the capsule endoscope swallowed doesn't proceed in a constant direction within the body. For example, assume that a user wants to obtain images of a cardiac portion of the stomach passing behind the esophagus to observe this portion downwardly after a patient swallows the capsule endoscope. In this case, when the capsule endoscope proceeds inside the body with the imaging direction headed reversely (upward or in a trailing direction), the capsule endoscope may not meet this desire.

In these days, a pantoscopic (or binocular) capsule endoscope which may obtain images in the both backward and forward direction (at the both ends) is also proposed in United States Patent Application Publication No. 2004/199061. According to the pantoscopic capsule endoscope, since the images in the backward and forward direction may be obtained in the forwarding direction, it does not matter that the capsule endoscope proceeds in any direction.

In the case of the pantoscopic capsule endoscope, however, a user has to observe a large amount of images obtained backward and forward on a display and the like later. Generally, even in the case of the monocular capsule endoscope, it takes a long time to observe images, and in the case of the pantoscopic endoscope, it takes an extravagant time. In the case of the pantoscopic capsule endoscope, the obtained image data is twice as much as that in the case of the monocular capsule endoscope through simple calculation, and it is necessary to transmit the data from the capsule endoscope to the receiver in a band wider than that of the monocular capsule endoscope, which increases restriction.

SUMMARY OF THE INVENTION

At least one object of the present invention is to solve the problems.

An in-vivo image capturing system according to one aspect of the present invention includes a capsule casing insertable into a subject from an oral cavity, the capsule casing including an imaging optical system capable of capturing images only in one end direction; an analyzing unit which analyzes image components captured by the imaging optical system within the oral cavity; and a warning unit which issues a warning to a user about a direction of the capsule casing based on the analytical result by the analyzing unit.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Preferred embodiments of an in-vivo image capturing apparatus and an in-vivo image capturing system according to the invention will be described in detail below with reference to the drawings. The invention is not limited to the embodiments and various changes may be made without departing from the scope of the invention.

Figure 1:
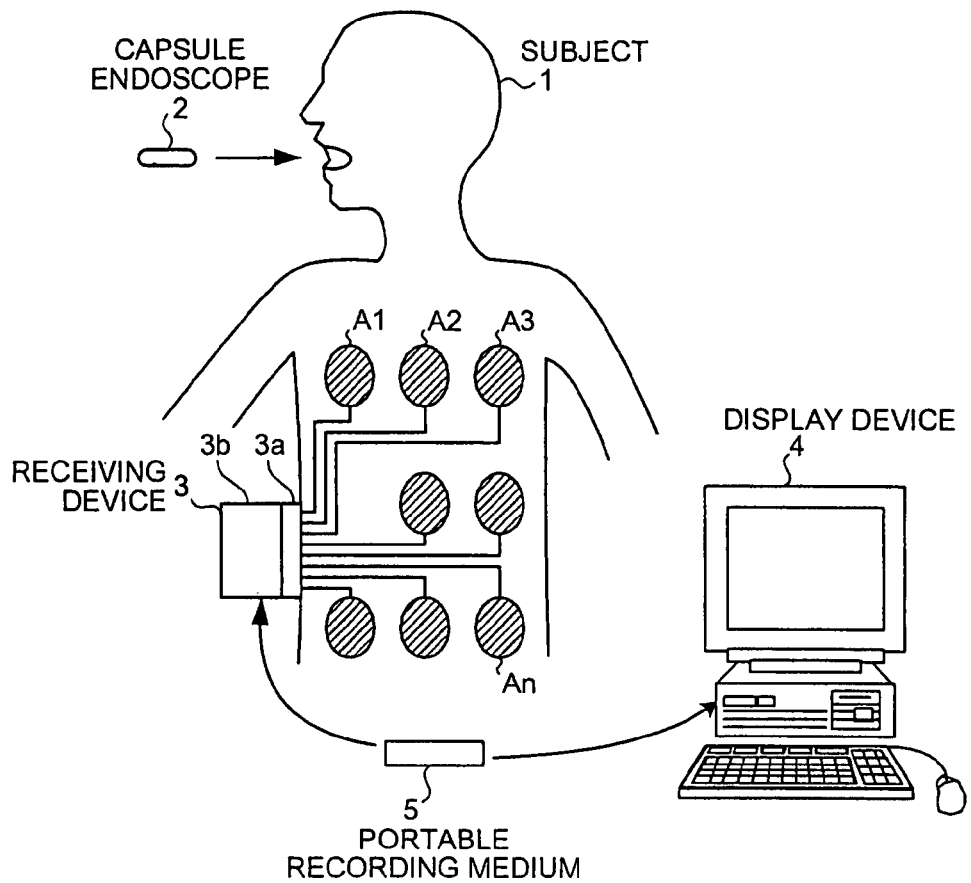
FIG. 1 is a schematic diagram showing the entire configuration of a radio in-vivo information acquiring system that is a preferred embodiment of an in-vivo image capturing system according to the invention.

FIG. 1 is a schematic diagram showing the whole structure of a radio in-vivo information acquiring system that is a preferred embodiment of the in-vivo image capturing system according to the invention. The in-vivo information acquiring system uses a capsule endoscope as one example of the in-vivo image capturing system. In FIG. 1, the in-vivo information acquiring system comprises a capsule endoscope 2 which is inserted into a subject 1 in order to obtain images inside the body cavity and transmit data such as an image signal, and a receiving device 3 which is used for receiving processing of radio signals transmitted from the capsule endoscope 2 inserted into the subject 1. The receiving device 3 is used while being carried with the subject 1, to perform the processing of receiving the radio signals received from the capsule endoscope 2.

The in-vivo information acquiring system according to the embodiment further includes a display device 4 which displays the images inside the body cavity according to the image signals received by the receiving device 3 and a portable recording medium 5 for exchanging the data between the receiving device 3 and the display device 4. The receiving device 3 has an antenna unit 3a including a plurality of receiving antennas A1 to An attached to the external surface of the subject 1 and a main receiving unit 3b which processes radio signals received through the antenna unit 3a. These units 3a and 3b are connected together through a connector in a removable way. The receiving antennas A1 to An are attached to, for example, a receiving jacket which the subject 1 may put on and off and the subject 1 may be provided with the receiving antennas A1 to An through wearing the receiving jacket. In this case, the receiving antenna A1 to An may be removable from the jacket.

The display device 4 is to display the images inside the body cavity obtained by the capsule endoscope 2 and it is formed in a workstation which displays the images based on the data obtained by the portable recording medium 5 and the like. Specifically, the display device 4 may be formed to display the images directly like a CRT display and a liquid crystal display and may be formed to output the images to another medium like a printer.

A CompactFlash® memory or the like is used as the portable recording medium 5, it is attachable to and detachable from the receiving device 3 and the display 7, and it may output or record information when it is inserted to the both. In the first embodiment, for example, before an examination, the portable recording medium 5 is inserted to the display device 4 of the workstation to store identification information such as an examination ID therein. Just before the examination, the portable recording medium 5 is inserted to the receiving device 3, and the receiving device 3 reads the identification information and registers it therein. While the capsule endoscope 2 is moving inside the body cavity of the subject 1, the portable recording medium 5 is inserted to the receiving device 3 attached to the subject 1 and records data transmitted from the capsule endoscope 2. After the capsule endoscope 2 is naturally excreted from the subject 1, in other words, after the imaging inside the subject 1 is completed, the portable recording medium 5 is taken out from the receiving device 3 and inserted to the display device 4, so that the display device 4 read the data recorded in the portable recording medium 5. Transfer of the data between the receiving device 3 and the display device 4 is performed by the portable recording medium 5, thereby enabling the subject 1 to move freely during the imaging of the inside of the body cavity and contributing to shorten the time of data transfer between the receiving device 3 and the display device 4. Another recording device built in the receiving device 3, for example, a hard disk may be used in order to transfer the data from the receiving device 3 to the display device 4, with the both connected with or without wire.

Figure 2:
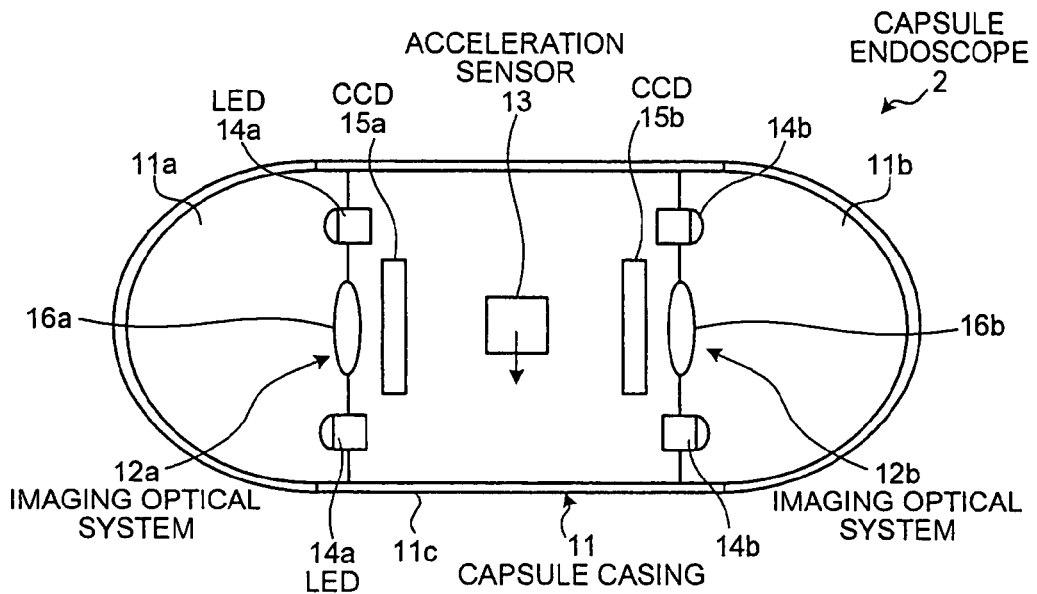
FIG. 2 is a longitudinal section view showing a schematic configuration of a capsule endoscope shown in FIG. 1.

The capsule endoscope 2 will be described with reference to FIG. 2. FIG. 2 is a longitudinal sectional view showing a schematic configuration of the capsule endoscope 2 shown in FIG. 1. As shown in FIG. 2, the capsule endoscope 2 according to the first embodiment is formed as a pantoscopic type, comprising a capsule casing 11 insertable into the body cavity of the subject 1, two imaging optical systems 12a and 12b which are built in the capsule casing 11 in order to obtain images in the backward and forward direction at its both ends. The capsule endoscope 2 includes an acceleration sensor 13 as a gravity sensor as well as a battery, circuit components, and an antenna which are not illustrated.

The capsule casing 11 is of a size swallowable from the oral cavity into the body of the subject 1. The capsule casing 11 is formed into an outer case which is sealed off a liquid by elastically fitting substantially hemispheric, transparent or translucent front covers 11a and 11b to a cylindrical body cover 11c made of a colored material which does not allow the visible light to pass through.

The imaging optical system 12a within the capsule casing 11 includes a plurality of light emitting elements 14a (hereinafter, referred to as "LED 14a") which emit illumination light for illuminating a portion of the subject within the body cavity through the front cover 11a, an imaging device 15a (hereinafter, referred to as "CCD 15a") such as CCD or CMOS which, upon receipt of the reflected light of the illumination light, images the portion of the subject, and an image forming lens 16a which forms an image of a target on the CCD 15a. The imaging optical system 12a can obtain images in the direction of an end at the side of the front cover 11a.

The imaging optical system 12b within the capsule casing 11 includes a plurality of light emitting elements 14b (hereinafter, referred to as "LED 14b") which emit illumination light for illuminating a portion of the subject within the body cavity through the front cover 11b, an imaging device 15b (hereinafter, referred to as "CCD 15b") such as CCD or CMOS which, upon receipt of the reflected light of the illumination light, images the portion of the subject, and an image forming lens 16b which forms an image of a target on the CCD 15b. The imaging optical system 12b can obtain images in the direction of the other end at the side of the front cover 11b.

The acceleration sensor 13 is to detect the gravity direction of the capsule casing 11 inserted into the body cavity of the subject 1 by using the gravity acceleration and it is arranged, for example, in the central portion of the capsule casing 11. The positional relationship between the acceleration sensor 13, and the CCDs 15a and 15b is set and stored in advance, which makes it possible to specify which of the CCDs 15a and 15b is positioned at the side of the gravity direction detected by the acceleration sensor 13.

Figure 3:
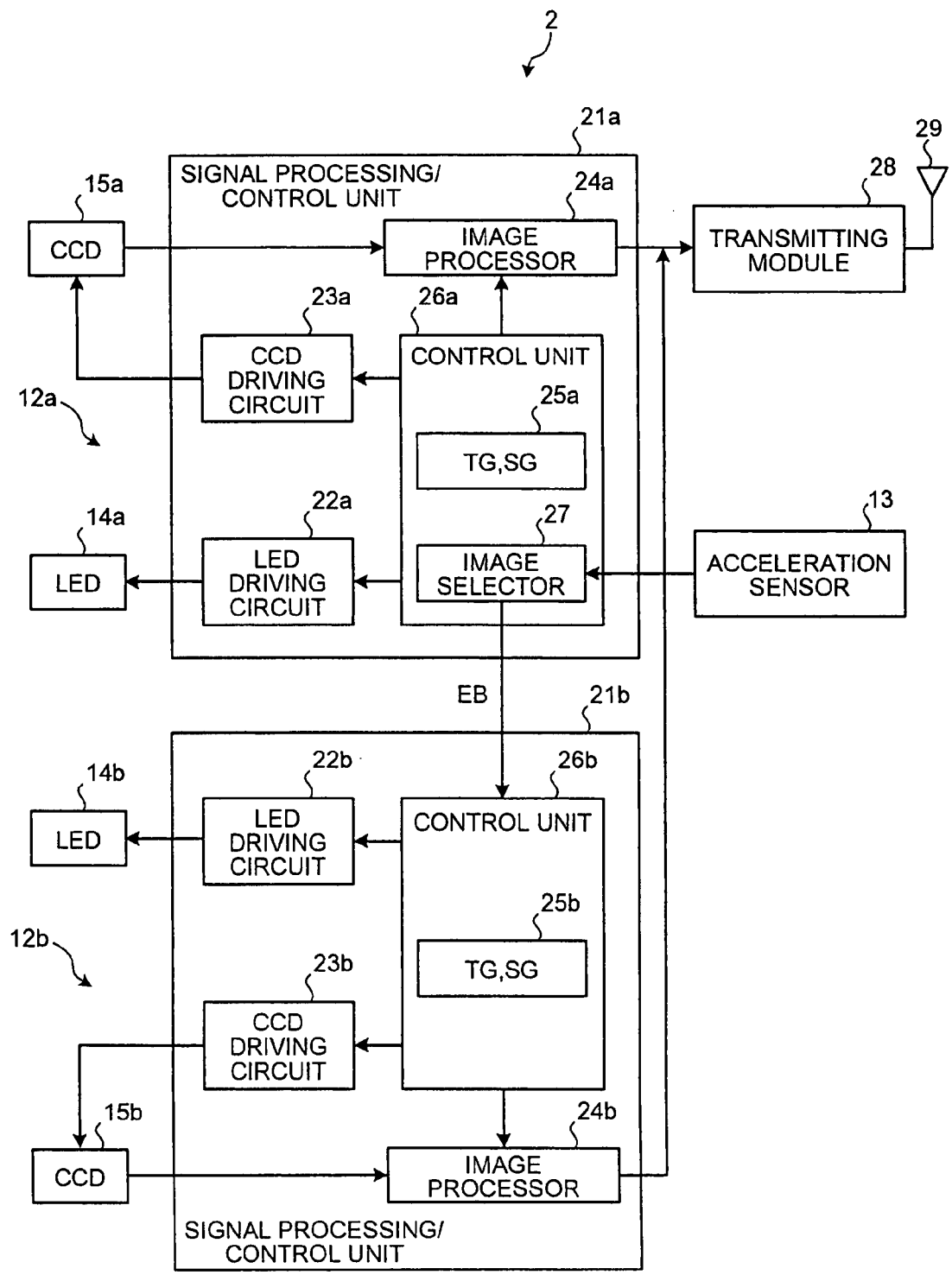
FIG. 3 is a schematic block diagram showing the internal circuit configuration of the capsule endoscope.

Next, the internal circuit configuration of the capsule endoscope 2 will be described with reference to FIG. 3. FIG. 3 is a schematic block diagram showing the internal circuit configuration of the capsule endoscope 2. First, a signal processing/control unit 21a is to control the LED 14a and the CCD 15a which make a pair, and the unit 21a has an LED driving circuit 22a and a CCD driving circuit 23a corresponding to the LED 14a and the CCD 15a, respectively. The signal processing/control unit 21a has an image processor 24a which performs predetermined image processing including correlated double sampling processing, amplification processing, A/D converting processing and multiplexing processing on output signals supplied from the CCD 15a. The signal processing/control unit 21a includes a control unit 26a having a timing generator (TG) and a sync generator (SG) 25a which generate various timing signals and synchronization signals. The signal processing/control unit 21a controls the operations and the operational timing of the driving circuits 22a and 23a and the image processor 24a according to the timing signals and the synchronization signals generated by the timing generator and the sync generator 25a.

A signal processing/control unit 21b is to control the LED 14b and the CCD 15b which make a pair, and it has an LED driving circuit 22b and a CDD driving circuit 23b corresponding to the LED 14b and the CCD 15b, respectively. The signal processing/control unit 21b has an image processor 24b which performs predetermined image processing including a correlated double sampling processing, amplification processing, A/D converting processing and multiplexing processing on output signals supplied from the CCD 15b. The signal processing/control unit 21b includes a control unit 26b having a timing generator (TG) and a sync generator (SG) 25b which generate various timing signals and synchronization signals. The signal processing/control unit 21b controls the operations and the operational timing of the driving circuits 22b and 23b and the image processor 24b according to the timing signals and the synchronization signals generated by the timing generator and the sync generator 25b.

The control units 26a and 26b are in a relationship of master to servant; the control unit 26a is a master and the control unit 26b is a slave. The control unit 26b carries out the control operations in accordance with the control unit 26a only that during the time when an enable signal EB from the control unit 26a is at H level. The control unit 26a includes an image selector 27 which selects one of the imaging optical system 12a and the imaging optical system 12b to operate according to the detected result of the gravity direction of the capsule casing 11 detected by the acceleration sensor 13. In the first embodiment, the forwarding direction (gravity direction) of the capsule endoscope 2 is a desired imaging direction. When the gravity direction detected by the acceleration sensor 13 is at the side of the front cover 11a, the image selector 27 controls the LED 14a and the CCD 15a to operate so that the imaging optical system 12a obtains the images. When the gravity direction detected by the acceleration sensor 13 is at the side of the front cover 11b, the image selector 27 sets the enable signal EB at the H level to control the LED 14b and the CCD 15b to operate so that the imaging optical system 12b obtains the images.

The capsule endoscope 2 includes a transmitting module 28 and a transmitting antenna 29 which are provided on an output path of imaging data having passed through the image processors 24a and 24b in order to output RF modulation signals.

Figure 4A:
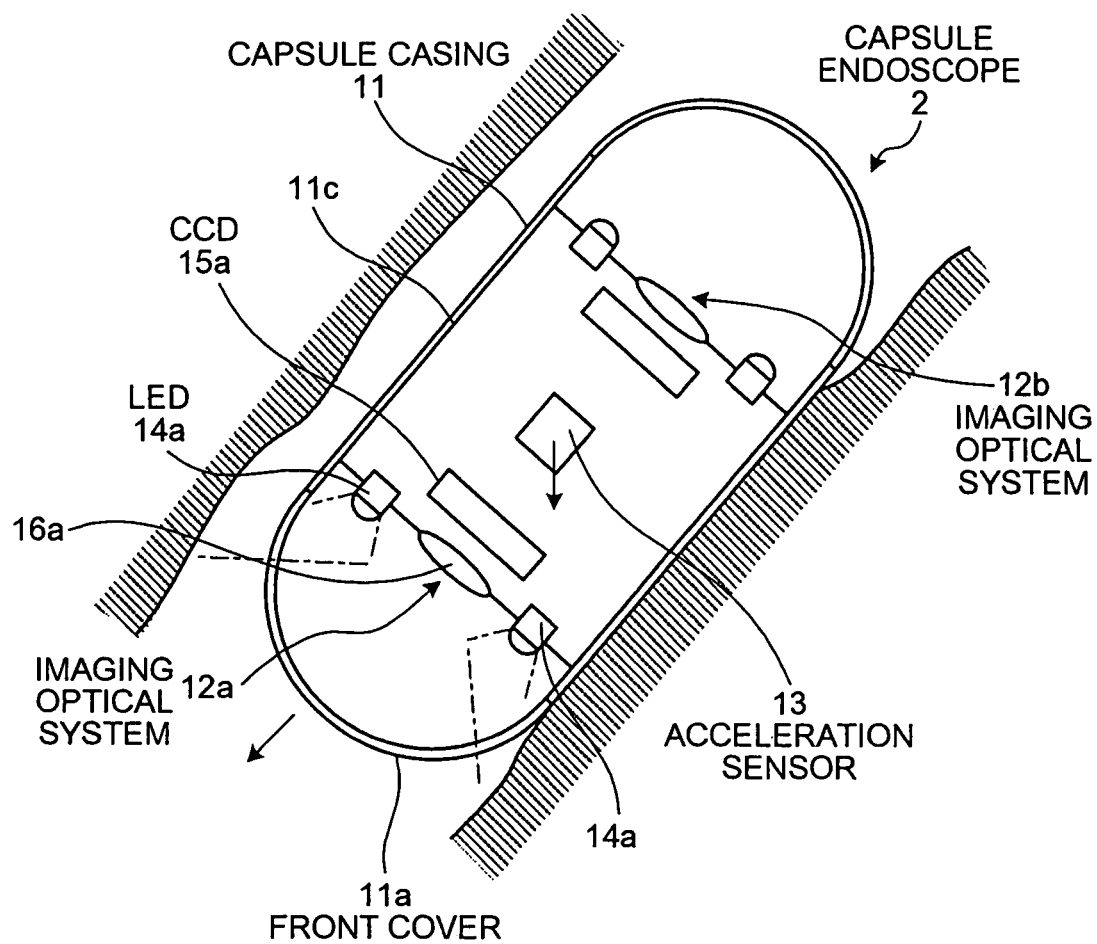
FIG. 4A is a longitudinal section view showing one progress example of the capsule endoscope within a body cavity.

After the capsule endoscope 2 (capsule casing 11) is inserted into the subject 1, it moves inside the body cavity with the front cover 11a or the front cover 11b headed in the processing direction. For example, as shown in FIG. 4A, the case will be described, in which the endoscope proceeds inside the body cavity of the subject 1 with the front cover 11a headed downwardly. In this case, as shown by the arrow in FIG. 4, the acceleration sensor 13 detects that the gravity direction of the capsule casing 11 is toward the side of the front cover 11a. According to the detected result of the gravity direction by the acceleration sensor 13, the image selector 27 selects only the imaging optical system 12a at this side and the control unit 26a controls the driving circuits 22a and 23a to turn on the LED 14a and activate the CCD 15a to obtain the images. In this manner, the capsule endoscope 2 obtains only the images of the body cavity downwardly viewed from the side of the front cover 11a in the forwarding direction, and transmits imaging data to the receiving device 3 through the transmitting module 28 and the transmitting antenna 29 after the image processor 24a processes the imaging data.

Figure 4B:
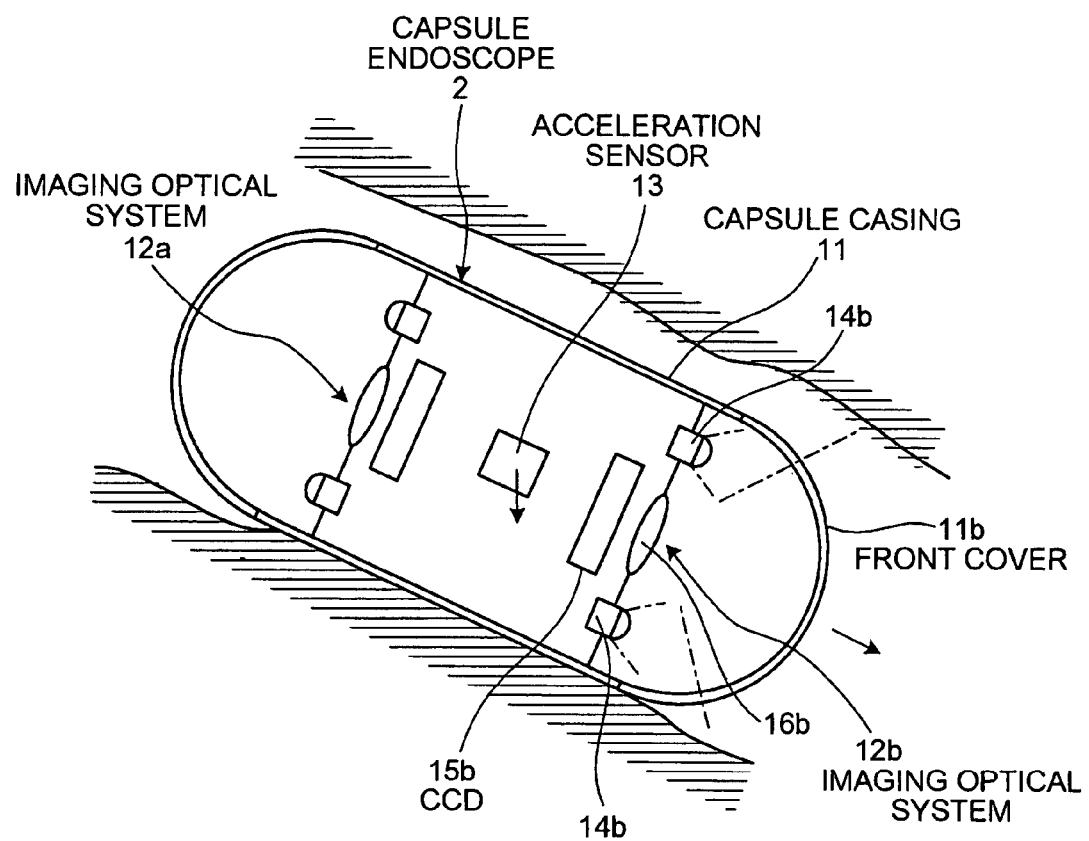
FIG. 4B is a longitudinal section view showing another progress example of the capsule endoscope within a body cavity.

On the other hand, as shown in FIG. 4B, when the endoscope processes inside the body cavity of the subject 1 with the front cover 11b headed downwardly, the acceleration sensor 13 detects that the gravity direction of the capsule casing 11 is toward the side of the front cover 11b as shown by the arrow in FIG. 4B. According to the detected result of the gravity direction by the acceleration sensor 13, the image selector 27 sets the enable signal EN from the control unit 26a to the control unit 26b at the H level in order to select only the imaging optical system 12b, and the control unit 26b controls the driving circuits 22b and 23b to turn on the LED 14b and activate the CCD 15b to obtain the images. Thus, the capsule endoscope 2 obtains only the images of the body cavity downwardly viewed from the side of the front cover 11b in the forwarding direction, and transmits imaging data to the receiving device 3 through the transmitting module 28 and the transmitting antenna 29 after the image processor 24b processes the imaging data.

According to the pantoscopic capsule endoscope 2 capable of obtaining images in the directions of its both ends according to the first embodiment, the gravity direction of the capsule casing 11 within the subject 1 is detected by the acceleration sensor 13, and according to the detected result, the imaging optical system 12a or 12b is selected to obtain the images such that the gravity direction side, a desired direction, is always in the imaging direction. Therefore, even when the capsule casing 11 proceeds with any of the distal and covers 11a and 11b headed downwardly, and even when it turns upside down on the way, it is possible to obtain images always downwardly viewed in the forwarding direction, within the subject 1. Since the upward images in the trailing direction are not obtained, the amount of the image data and the observation time may be substituted even in the pantoscopic type to the same degree as that of the monocular type.

Figure 5:
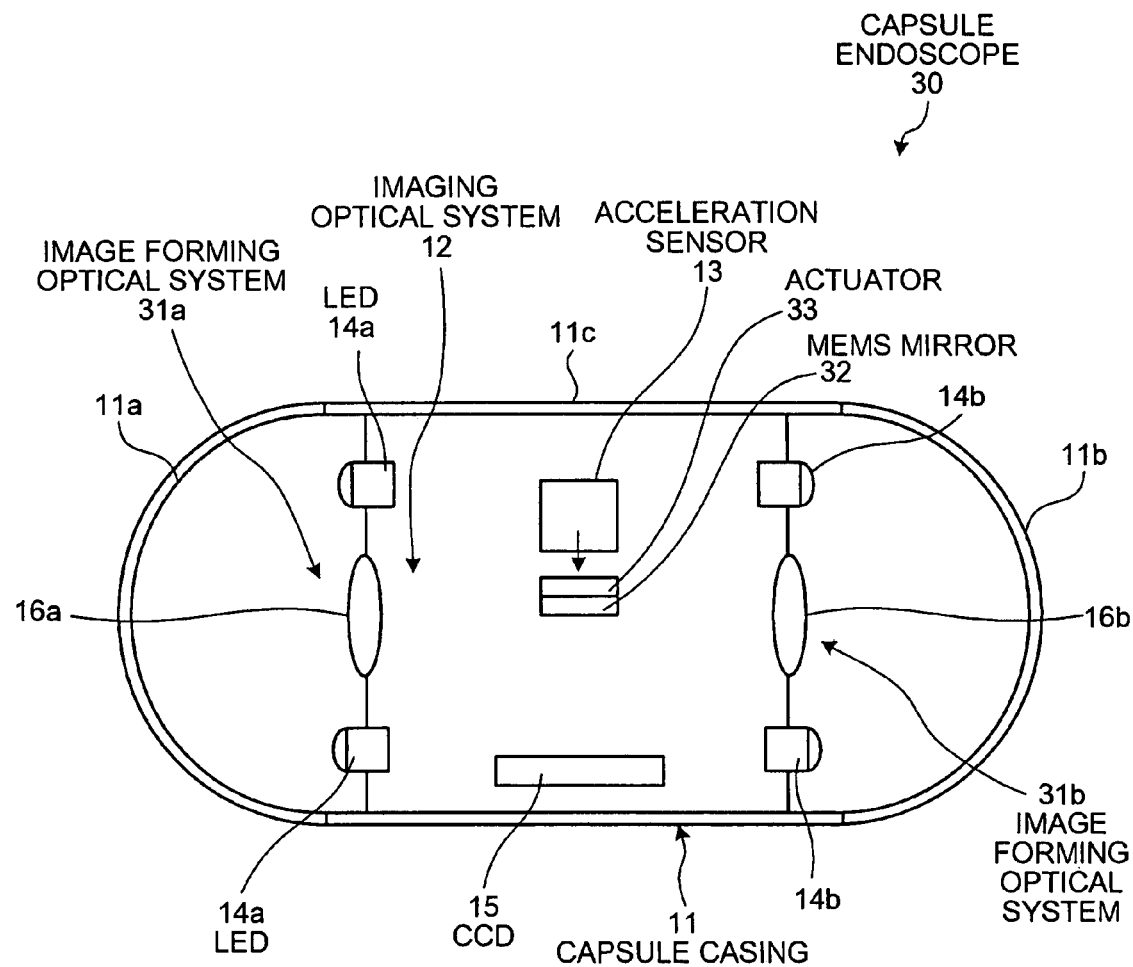
FIG. 5 is a longitudinal section view showing a schematic configuration of a capsule endoscope according to a second embodiment of the invention.

FIG. 5 is a longitudinal sectional view showing a schematic configuration of a capsule endoscope 30 according to a second embodiment of the invention. The capsule endoscope 30 according to the second embodiment is a pantoscopic capsule endoscope comprising one CCD 15 which is shared for obtaining images in the directions of the both ends instead of the CCDs 15a and 15b of the capsule endoscope 2 shown in FIG. 2. The LED 14a and the image forming lens 16a configure an image forming optical system 31a for forming the obtained images of the side of the front cover 11a on the CCD 15, while the LED 14b and the image forming lens 16b configure an image forming optical system 31b for forming the obtained images of the side of the front cover 11b on the CCD 15. The endoscope 30 includes a micro electro mechanical system (MEMS) mirror 32 as a switching mirror which selectively switch only one of the image forming optical system 31a and the image forming optical system 31b through displacement on the common optical path to the CCD 15. The MEMS mirror 32 is driven by an actuator 33 such as a piezoelectric element to switch the optical path. That is, an imaging optical system 12 according to the second embodiment is formed by one CCD 15, two image forming optical systems 31a and 31b, and the MEMS mirror 32. The other configuration is the same as that in the case of the capsule endoscope 2, also including the acceleration sensor 13. The acceleration sensor 13 may be formed as a MEMS acceleration sensor similarly to the MEMS mirror 32.

Figure 6:
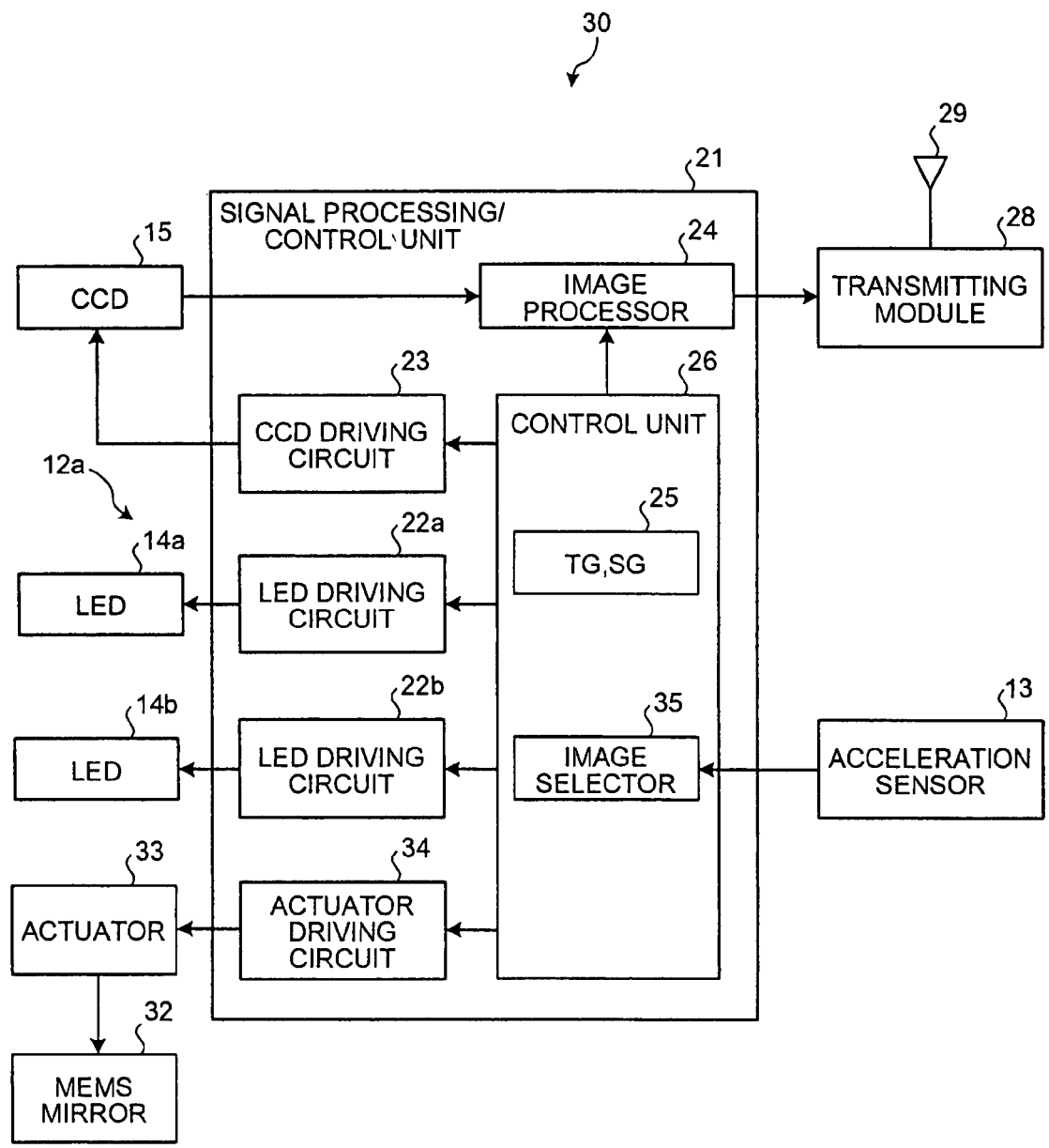
FIG. 6 is a schematic block diagram showing an internal circuit structure of the capsule endoscope.

Next, an internal circuit configuration of the capsule endoscope 30 will be described with reference to FIG. 6. FIG. 6 is a schematic block diagram showing the internal circuit configuration of the capsule endoscope 30. A signal processing/control unit 21 is to control the LEDs 14a and 14b within the image forming optical systems 31a and 31b, the common CCD 15 and the actuator 33 for the MEMS mirror 32. The signal processing/control unit 21 has the LED driving circuits 22a and 22b, a CCD driving circuit 23 and an actuator driving circuit 34 respectively corresponding to the LEDs 14a and 14b, the CCD 15 and the actuator 33. The signal processing/control unit 21 has an image processor 24 which performs predetermined image processing including a correlated double sampling processing, amplification processing, A/D converting processing, and multiplexing processing on output signals supplied from the CCD 15. The signal processing/control unit 21 also includes a control unit 26 having a timing generator (TG) and a sync generator (SG) 25 which generate various timing signals and synchronization signals. The signal processing/control unit 21 controls the operations and the operational timing of the driving circuits 22a, 23b, 23, and 34 and the image processor 24 according to the timing signals and the synchronization signals generated by the timing generator and the sync generator 25.

The control unit 26 includes an image selector 35 which selects one of the image forming optical system 31a and the image forming optical system 31b to operate according to the detected result of the gravity direction of the capsule casing 11 detected by the acceleration sensor 13. In the second embodiment, the forwarding direction (gravity direction side) of the capsule endoscope 30 is a desired imaging direction. When the gravity direction detected by the acceleration sensor 13 is at the side of the front cover 11a, the image selector 35 drives the actuator 33 to displace the MEMS mirror 32 in order to activate the image forming optical system 31b. In parallel with this, it controls the LED 14a to operate so that the image forming optical system 31a and the CCD 15 obtain the images. On the other hand, when the gravity direction detected by the acceleration sensor 13 is at the side of the front cover 11b, the image selector 35 drives the actuator 33 to displace the MEMS mirror 32 in order to activate the image forming optical system 31b. In parallel with this, it controls the LED 14b to operate so that the image forming optical system 31b and the CCD 15 obtain the images. Here, it is preferable that the timing of displacing the MEMS mirror 32 is adjusted at the timing when the CCD 15 is not capturing the images.

Figure 7A:
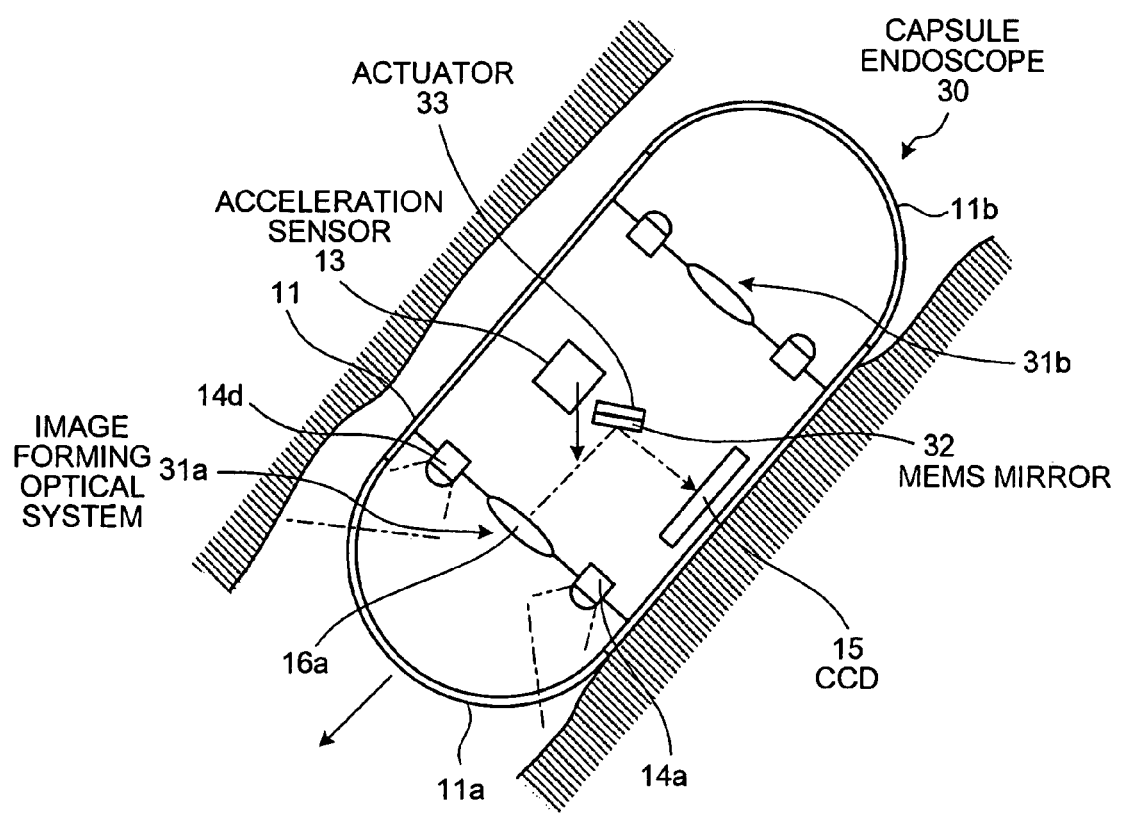
FIG. 7A is a longitudinal section view showing one progress example of the capsule endoscope within a body cavity.

After the capsule endoscope 30 (capsule casing 11) is inserted into the subject 1, it moves inside the body cavity with the front cover 11a or the front cover 11b headed in the proceeding direction. For example, as shown in FIG. 7A, the case will be described, in which the endoscope proceeds inside the body cavity of the subject with the front cover 11a headed downwardly. In this case, the acceleration sensor 13 detects that the gravity direction of the capsule casing 11 is toward the side of the front cover 11a as shown by the arrow in FIG. 7A. Upon receipt of the detected result of the gravity direction by the acceleration sensor 13, the image selector 35 drives the actuator 33 to displace the MEMS mirror 32 in order to activate only the image forming optical system 31a as shown in FIG. 7A, and the control unit 26 controls the driving circuit 22a and 23 to turn on the LED 14b and activate the CCD 15 to obtain the images. Thus, the capsule endoscope 30 obtains only the images of the body cavity downwardly viewed from the side of the front cover 11a in the forwarding direction, and transmits imaging data to the receiving device 3 through the transmitting module 28 and the transmitting antenna 29 after the image processor 24 processes the imaging data.

Figure 7B:
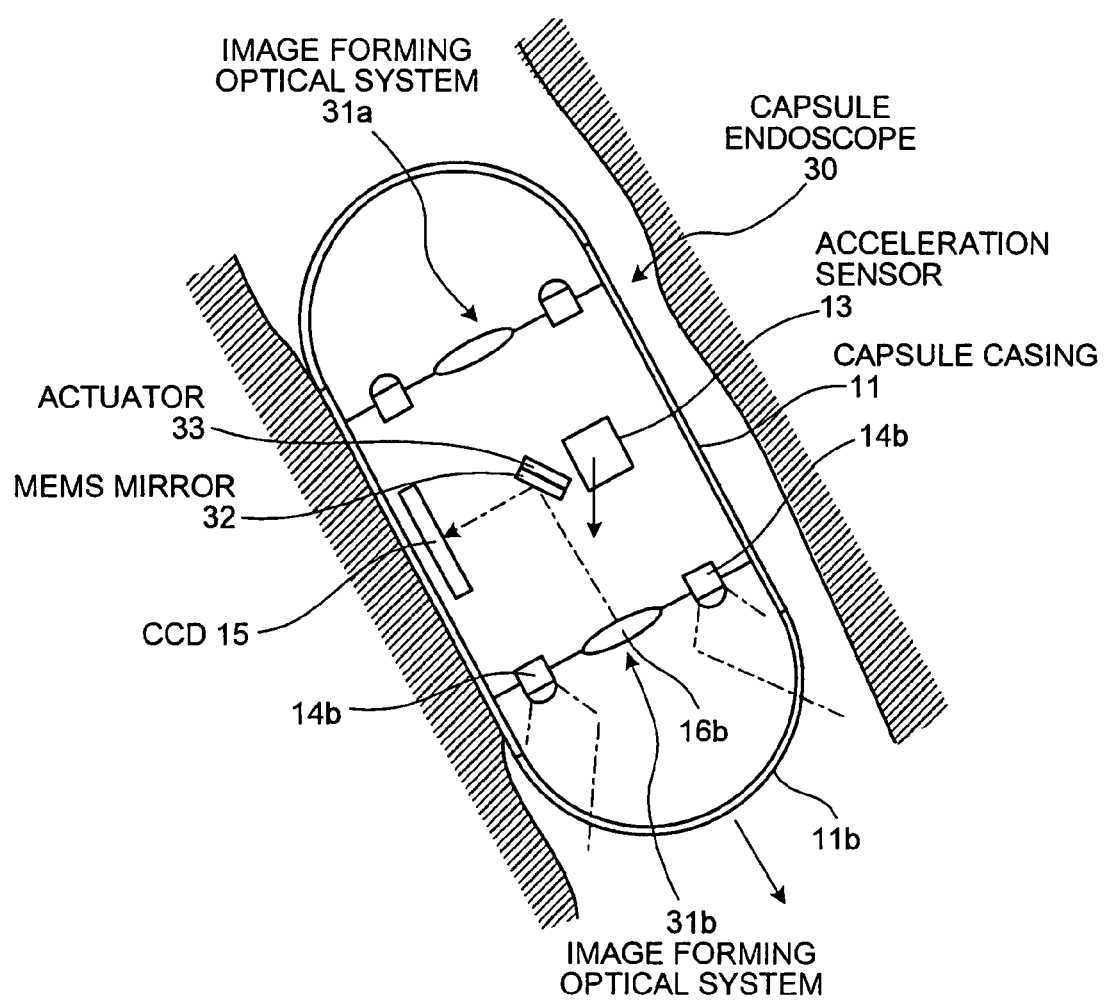
FIG. 7B is a longitudinal section view showing another progress example of the capsule endoscope within a body cavity.

On the other hand, as shown in FIG. 7B, when the endoscope proceeds inside the body cavity of the subject 1 with the front cover 11b headed downward, the acceleration sensor 13 detects that the gravity direction of the capsule casing 11 is toward the side of the front cover 11b as shown by the arrow in FIG. 7B. Upon receipt of the detected result of the gravity direction by the acceleration sensor 13, the image selector 35 drives the actuator 33 to displace the MEMS mirror 32 in order to activate only the image forming optical system 31b side as shown in FIG. 7B, and drives the driving circuit 22b and 23 for making the LED 14b put on the light so that the CCD 15 obtains the images under the control of the control unit 26. Therefore, the capsule endoscope 2 obtains only the images inside the body cavity in the downward front side as the front cover 11b side and after the imaging data processed by the image processor 24, it transmits the data to the receiving device 3 through the transmitting module 28 and the transmitting antenna 29.

In this way, according to the pantoscopic capsule endoscope 30 which can obtain images in the directions of the both ends according to the second embodiment, the gravity direction of the capsule casing 11 within the subject 1 is detected by the acceleration sensor 13, and according to the detected result, the image forming optical system 31a or 31b is activated by displacing the MEMS mirror 32 in a switched way such that the gravity direction as the desired direction always becomes the imaging direction. Therefore, even when the capsule casing 11 proceeds with any of the front covers 11a and 11b headed downward, and even when it turns upside down on the way, it is possible to obtain images always downwardly viewed in the forwarding direction within the subject 1. The CCD 15 is shared, thereby costing less, and it does not obtain the images upwardly in the trailing side. Therefore, the number of the image data and the observation time may be retained even in the pantoscopic type to the same degree as that of the monocular type.

In the first and second embodiments, the forwarding direction (gravity direction) of the capsule endoscopes 2 and 30 is fixed as the desired imaging direction, and according to the detected result of the gravity direction by the acceleration sensor 13, they are controlled to head the imaging direction toward the gravity direction. When the trailing side of the capsule endoscopes 2 and 30 (anti-gravity direction) is fixed as the desired imaging direction, they may be controlled to head the imaging direction toward the anti-gravity direction according to the detected result of the gravity direction by the acceleration sensor 13.

Figure 8A:
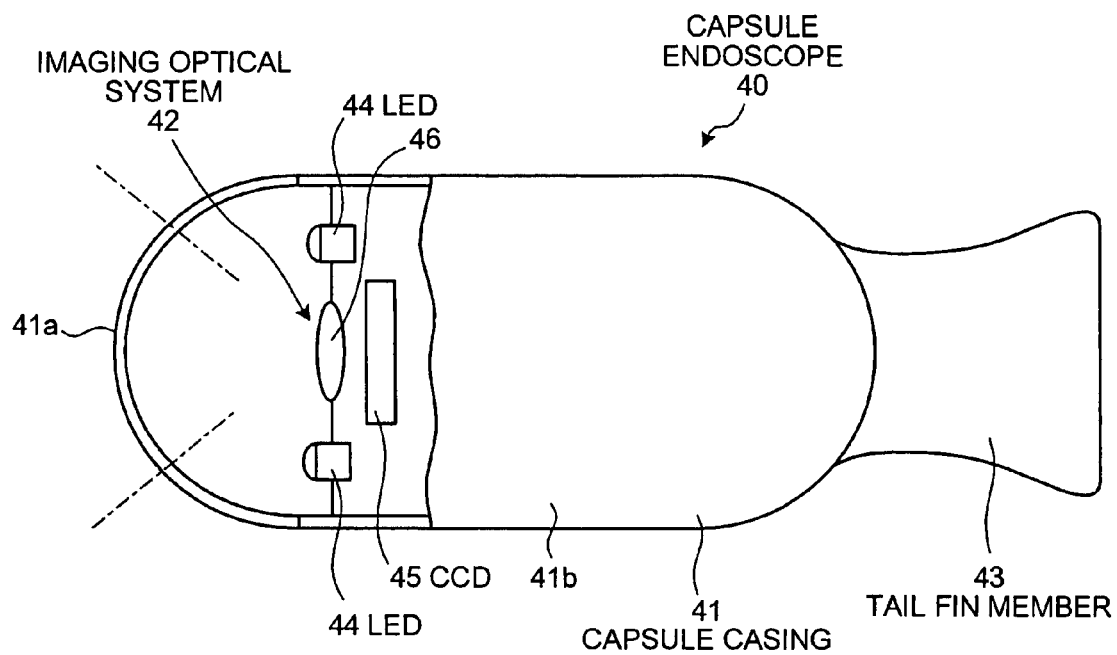
FIG. 8A is a lateral side view showing a schematic structure with one portion cut away from a capsule endoscope according to a third embodiment of the invention.
Figure 8B:
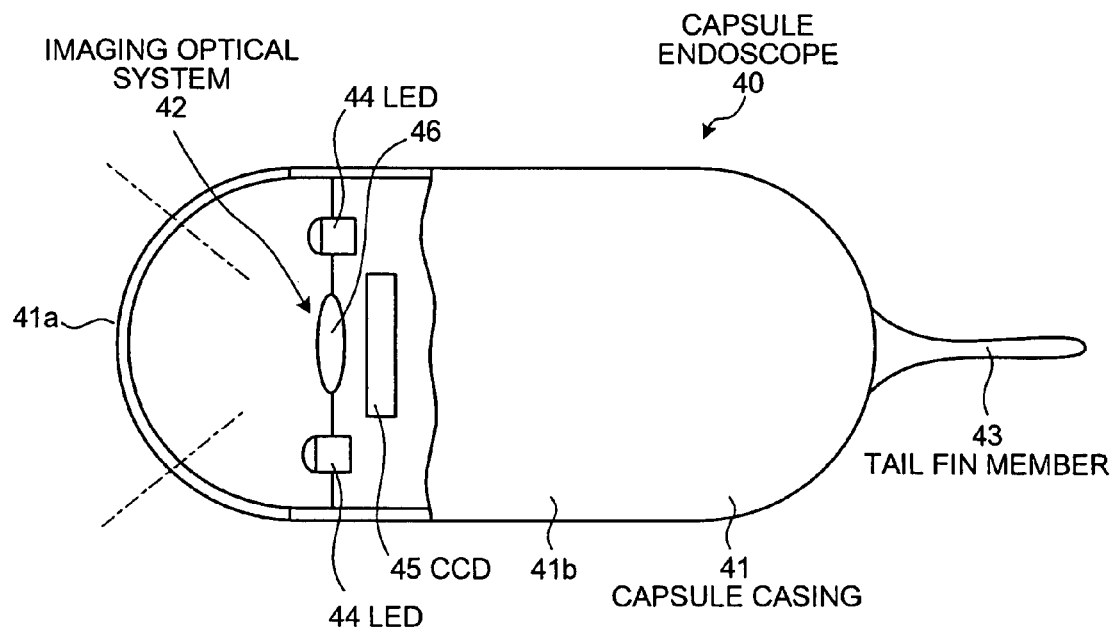
FIG. 8B is a plan view of FIG. 8A.

Next, a third embodiment of the invention will be described with reference to FIGS. 8A and 8B. FIG. 8A is a lateral side view showing a schematic configuration with one portion cut away from a capsule endoscope according to the third embodiment of the invention, and FIG. 8B is a plan view of FIG. 8A.

A capsule endoscope 40 according to the third embodiment is formed as the monocular type, comprising a capsule casing 41 which may be inserted into the body cavity of the subject 1 and an imaging optical system 42, built in the capsule casing 41, which can obtain images in only one direction. The capsule endoscope 40 has a tail fin member 43 as an orientation guide member provided at the other end of the capsule casing 41, in addition to a battery, circuit components, and an antenna which are not illustrated.

The capsule casing 41 is of a size swallowable from the oral cavity into the body of the subject 1. The capsule casing 41 is formed into an outer case which is sealed off a liquid by elastically fitting a substantially hemispheric, transparent or translucent front cover 41a to a cup-shaped body cover 41b made of a colored material which does not allow the visible light to pass through.

The imaging optical system 42 within the capsule casing 41 includes a plurality of light emitting elements 44 (hereinafter, referred to as "LED 44") which emit illumination light for illuminating a portion of the subject within the body cavity through the front cover 41a, an imaging device 45 (hereinafter, referred to as "CCD 45") such as CCD or CMOS which, upon receipt of the reflected light of the illumination light, images the portion of the subject, and an image forming lens 46 which forms an image of a target on the CCD 45. The imaging optical system 42 can obtain images only in the direction of one end at the side of the front cover 41a.

The tail fin member 43 is formed into a flat shape like a caudal fin and arranged in the rear end (the other end opposite to the front cover 41a) of the capsule casing 41, in order to orient the front cover 41a of the capsule casing 41 inserted into the body cavity of the subject 1 always forward.

According to the capsule endoscope 40 according to the third embodiment, the monocular capsule casing 41 capable of obtaining images only in one direction has, at the other side thereof, the tail fin member 43 which guides the capsule casing 41 to proceed within the subject 1 with its one end orientated always forward. Accordingly, when the subject 1 swallows the capsule endoscope 40 from the oral cavity in any side of the capsule endoscope, the tail fin member 43 moves in contact with the throat and the front cover 41a is orientated forward, thereby obtaining the images in the forward direction with it is fixed as the desired imaging direction in the monocular type.

The tail fin member 43 may be formed integrally with the capsule casing 41, or it may be formed by a separate member and attached to the rear side of the capsule casing 41. When the tail fin member 43 is made by the separate member, a material such as gelatin or oblaat which melts within the body cavity of the subject 1 may be used. When the separate member of the different material is retrofitted, preferably, the monocular capsule casing 41 is shipped as it is the ordinal capsule shape and it is attached to the casing just before the subject 1 swallows it.

Figure 9:
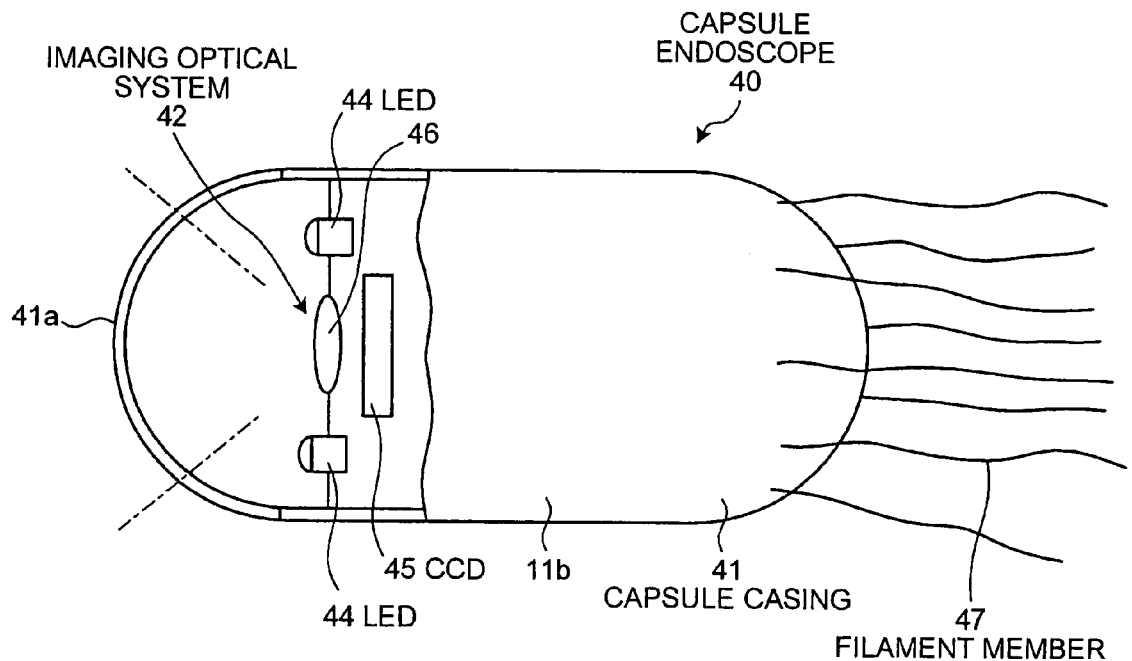
FIG. 9 is a lateral side view showing the schematic structure with one portion cut away from a capsule endoscope of a first modified example.

FIG. 9 is a lateral side view showing a schematic configuration with one portion cut away from a capsule endoscope of a first modified example. In the first modified example, a plurality of filament members 47 are set as the orientation guide member as a substitute for the tail fin member 43 of the capsule endoscope 40 as shown in FIGS. 8A and 8B. Because the filament members 47 are apt to stick to inside the oral cavity, swallowing with the front cover 41a side heading for the throat side is easy. Because the front cover 41a side is always orientated forward, it is possible to maintain the imaging forward as the desired imaging direction in the monocular type.

Figure 10:
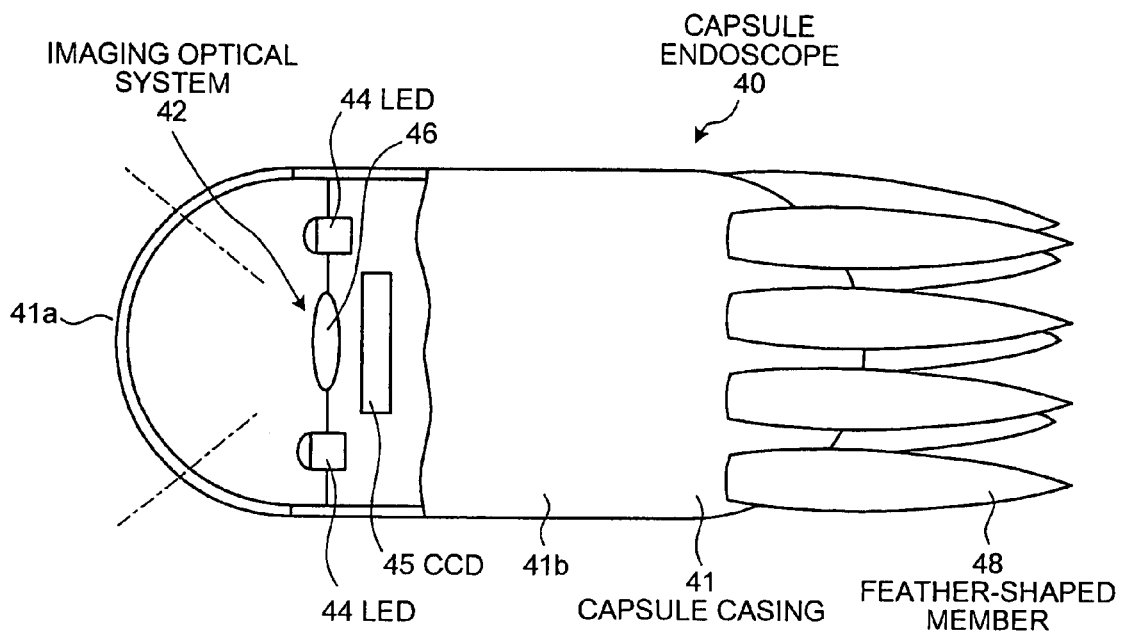
FIG. 10 is a lateral side view showing a schematic structure with one portion cut away from a capsule endoscope of a second modified example.

FIG. 10 is a lateral side view showing a schematic configuration with one portion cut away from a capsule endoscope of a second modified example. In the second modified example, a plurality of feather-shaped members 48 are attached to the capsule endoscope 40 as the orientation guide member instead of the tail fin member 43 as shown in FIGS. 8A and 8B. The feather-shaped members 48 are difficult to advance in the direction in which the feathers extend, and they prevent the capsule casing 41 from rotating within the tube of the internal organ of the subject 1. For this reason, the front cover 41a is always orientated forward, thereby obtaining the images in the forward direction with it is fixed as the desired imaging direction in the monocular type.

The filament members 47 and the feather-shaped members 48 according to the first and second modified examples may be formed integrally with the capsule casing 41, or they may be formed by a separate member and retrofitted to the rear side of the capsule casing 41.

Figure 11A:
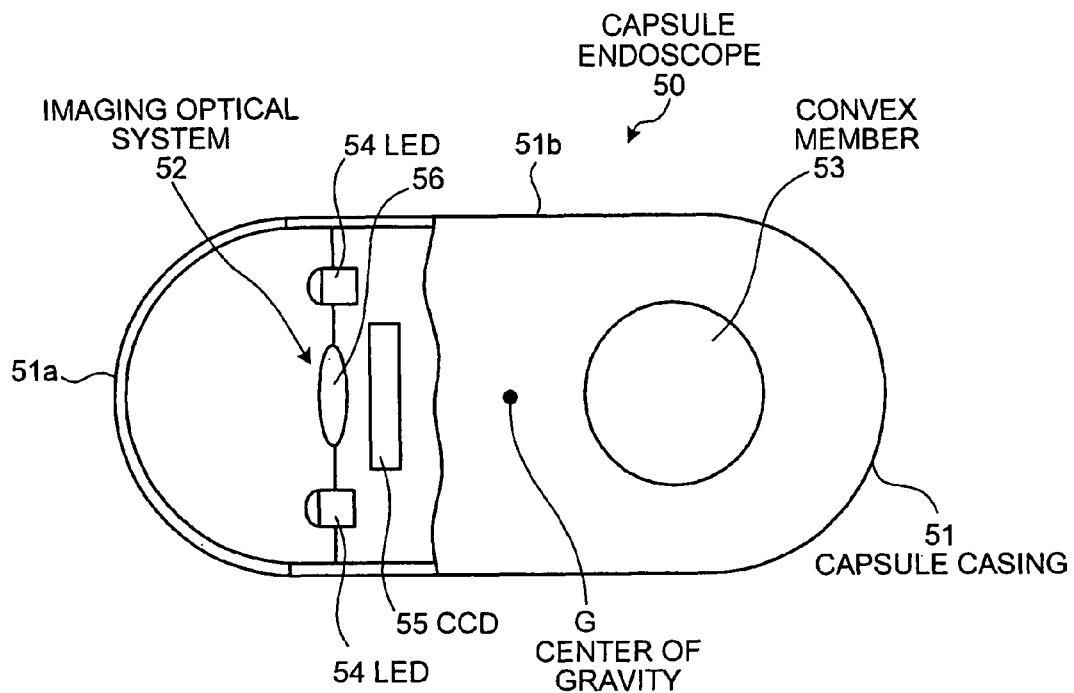
FIG. 11A is a lateral side view showing a schematic structure with one portion cut away from a capsule endoscope according to a fourth embodiment of the invention.
Figure 11B:
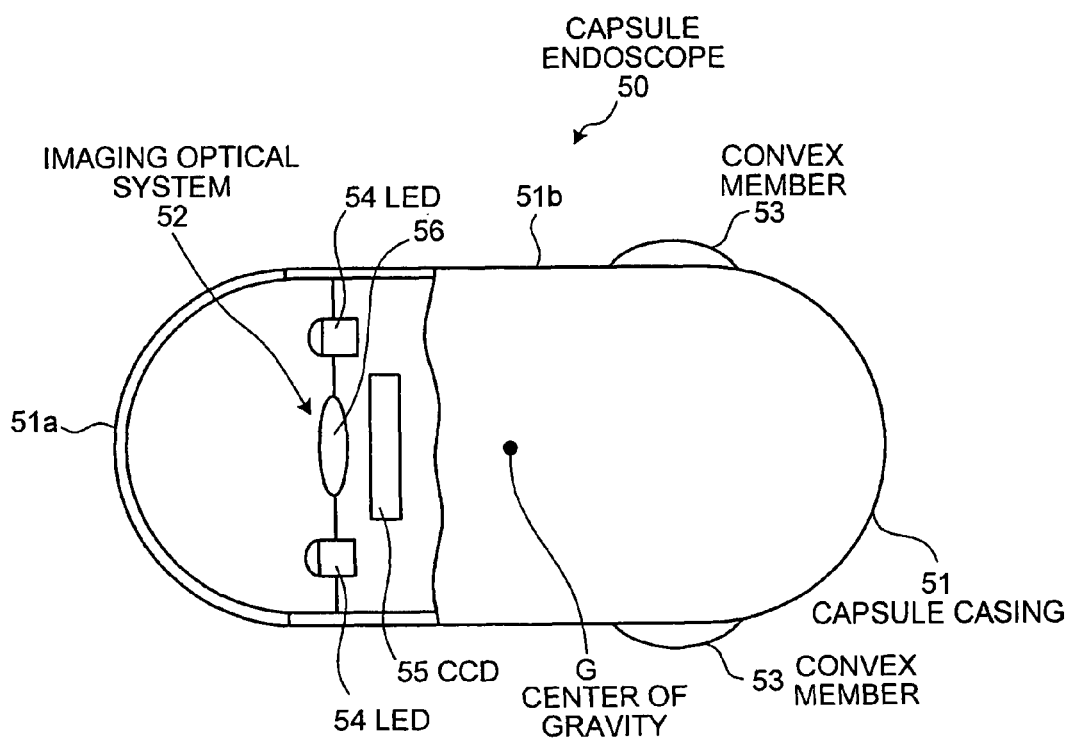
FIG. 11B is a plan view of FIG. 11A.

Next, a fourth embodiment of the invention will be described with reference to FIGS. 11A and 11B. FIG. 11A is a lateral side view showing a schematic configuration with one portion cut away from a capsule endoscope according to the fourth embodiment of the invention, and FIG. 11B is a plan view of FIG. 11A.

A capsule endoscope 50 according to the fourth embodiment is formed as the monocular type, comprising a capsule casing 51 which may be inserted into the body cavity of the subject 1 and an imaging optical system 52, built in the capsule casing 51, which can obtain images only in one direction. The capsule endoscope 50 has a pair of convex members 53 arranged in the both sides at the other end portion of the capsule casing 51, in addition to a battery, circuit components, and an antenna which are not illustrated.

The capsule casing 51 is of a size swallowable from the oral cavity into the body of the subject 1. The capsule casing 51 is formed into an outer case which is sealed off a liquid by elastically fitting a substantially hemispheric, transparent or translucent front cover 51a to a cup-shaped body cover 51b made of a colored material which does not allow the visible light to pass through.

The imaging optical system 52 within the capsule casing 51 includes a plurality of light emitting elements 54 (hereinafter, referred to as "LED 54") which emit illumination light for illuminating a portion of the subject within the body cavity through the front cover 51a, an imaging device 55 (hereinafter, referred to as "CCD 55") such as CCD or CMOS which, upon receipt of the reflected light of the illumination light, images the portion of the subject, and an image forming lens 56 which forms an image of a target on the CCD 55. The imaging optical system 52 can obtain images only in one direction at the side of the front cover 51a.

The pair of convex members 53 protrudes from the side surface of the capsule casing 51 in a hemispherical shape such that they may be a rotary axis for reversing the capsule casing 51 by coming into contact with the inner wall of the esophagus tube when the capsule casing 51 proceeds within the body cavity of the subject 1, especially within the esophagus. In the second embodiment, the forwarding direction of the capsule endoscope 50 is fixed as the desired imaging direction. For this reason, the pair of convex members 53 is arranged at the portion toward the other end (opposite to the front cover 51a) deviated from the center of gravity G set at the center of the capsule casing 51. In addition, the center of gravity G may be positioned not only at the center of the capsule casing 51 but also at a position deviated backward or forward from the center.

Figure 12A:
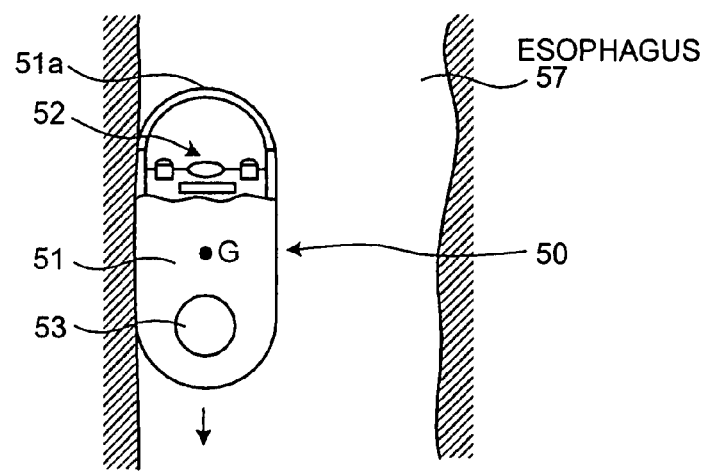
FIG. 12 is an explanatory view schematically showing the progress of the capsule endoscope within an esophagus.
Figure 12B:
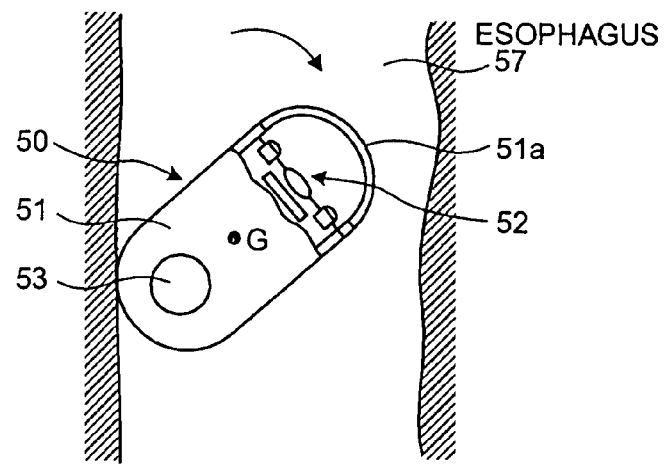
Figure 12C:
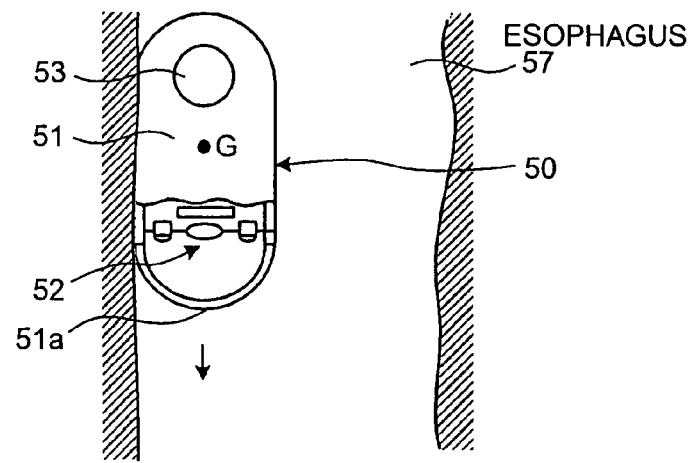

The case will be described, in which images of the cardiac portion of the stomach passing behind the esophagus are obtained downwardly for the observation after the capsule endoscope 50 is swallowed. FIGS. 12A to 12C are explanatory views schematically showing progress of the capsule endoscope 50 within an esophagus. In this case, even when the capsule endoscope 50 is swallowed with the imaging direction upward as shown in FIG. 12A, while it is falling down within the esophagus 57 of the subject 1, the pair of convex members 53 protruding from the side surface of the capsule casing 51 comes into contact with the inner wall of the esophagus 57 and may be the rotation axis. On the other hand, the center of gravity G of the capsule casing 51 is positioned at the upper position than the pair of convex members 53. Therefore, the capsule endoscope 50 is unstable and the capsule casing 51 rotates around the convex members 53 as the rotation axis upside down such that the center of gravity G is positioned at the lower position than the convex members 53 as shown in FIGS. 12B and 12C. Accordingly, the front cover 51a side is headed downward, thereby making it possible to obtain the images with the forwarding direction (downward) of the capsule endoscope 50 fixed as the desired imaging direction.

For example, as shown in FIG. 12C, when the capsule endoscope 50 is swallowed in the desired imaging direction, the capsule casing 51 does not rotate upside down owing to the positional relationship between the center of gravity G and the pair of convex members 53.

Only by making the center of gravity G of the capsule endoscope 50 closer to the front cover 51a, the front cover 51a may be headed downward when it moves downward in the esophagus 57. However, it does not have such a portion as the convex members 53, it is difficult to provide it with the rotation axis and difficult to rotate. Further, it becomes necessary to change the internal structure and the arrangement in order to deviate the center of gravity G, which causes much restriction. On the contrary, in the case of the fourth embodiment, it is easy to rotate with the center of gravity G remaining at the standard center position.

Figure 13A:
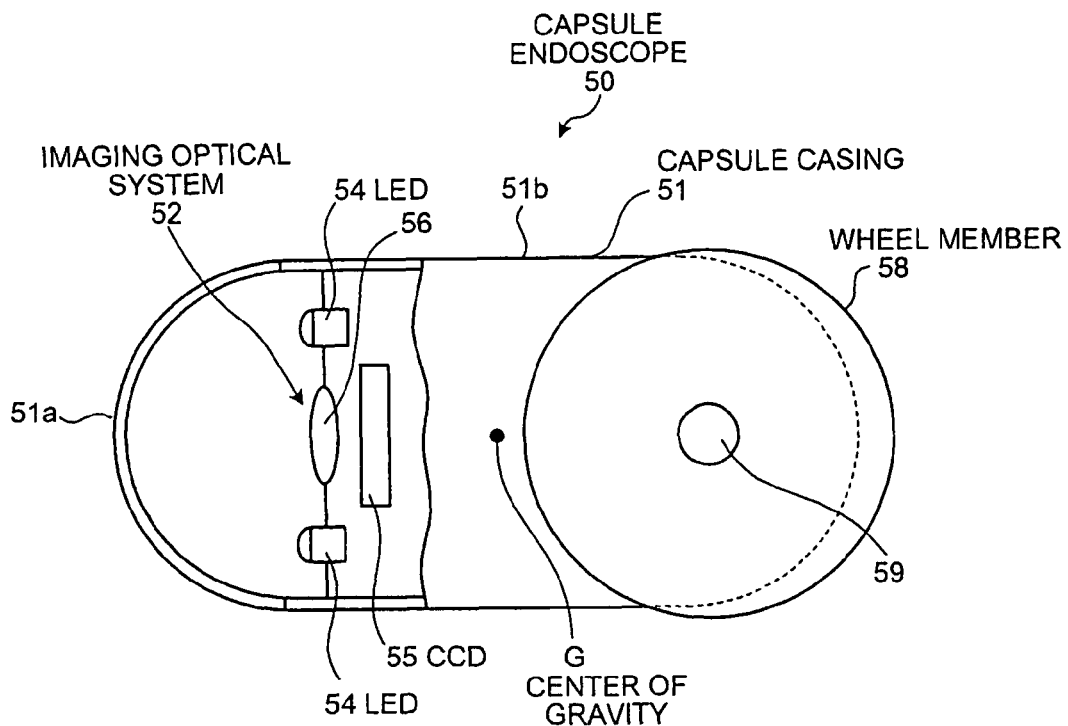
FIG. 13A is a lateral side view showing the schematic structure with one portion cut away from a capsule endoscope of a third modified example.
Figure 13B:
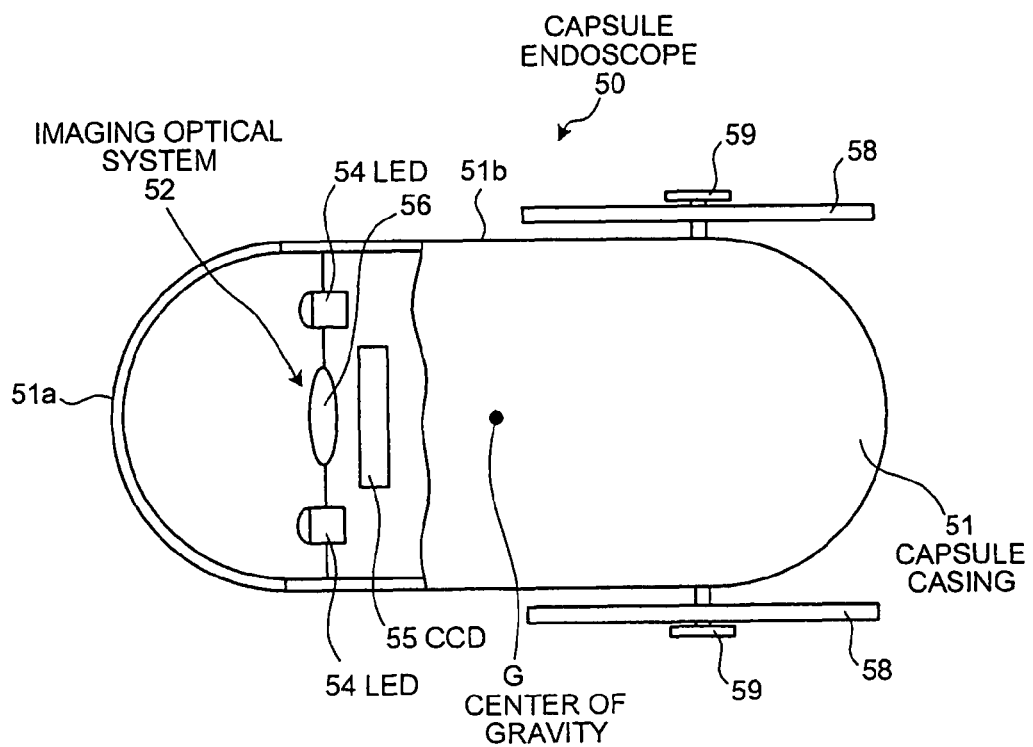
FIG. 13B is a plan view of FIG. 13A.

FIG. 13A is a lateral side view showing a schematic configuration with one portion cut away from a capsule endoscope of a third modified example, and FIG. 13B is a plan view of FIG. 13A. A capsule endoscope 50 according to the third modified example has a pair of wheel members 58 instead of the pair of convex members 53, as shown in FIGS. 11A and 11B. The pair of wheel members 58 is formed larger than the capsule casing 51 in diameter, and they can freely rotate around rotary shafts 59 respectively set in the both sides at the other end portion (opposite to the front cover 51a) away from the center of gravity G of the capsule casing 51. The center of gravity G may be positioned not only at the center of the capsule casing 51 but also at a position deviated backward or forward from the center.

Figure 14A:
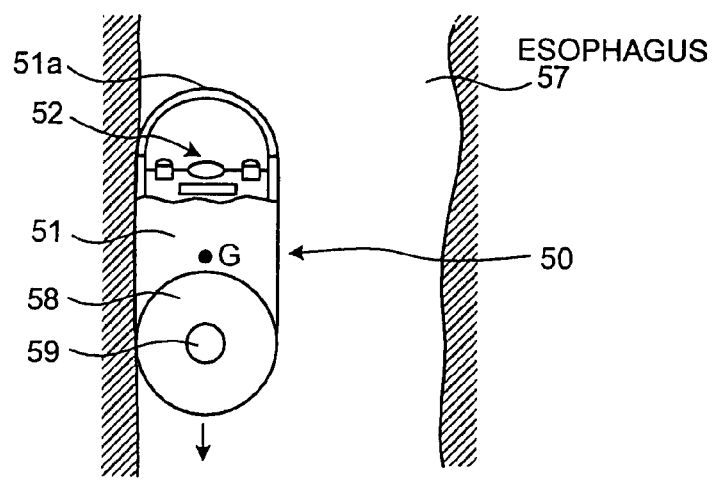
FIG. 14 is an explanatory view schematically showing the progress of the capsule endoscope within an esophagus.
Figure 14B:
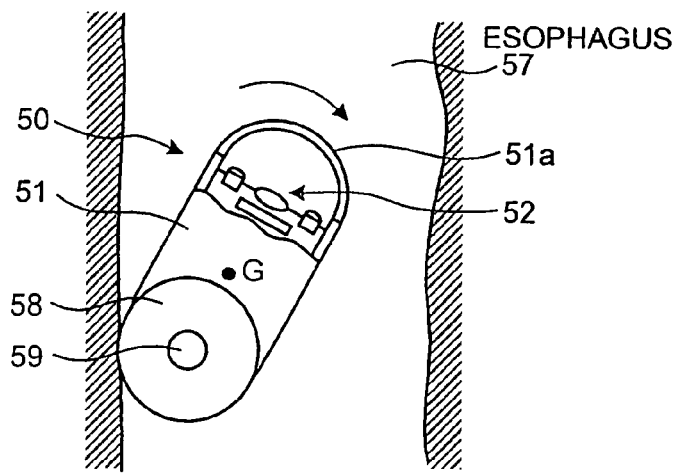
Figure 14C:
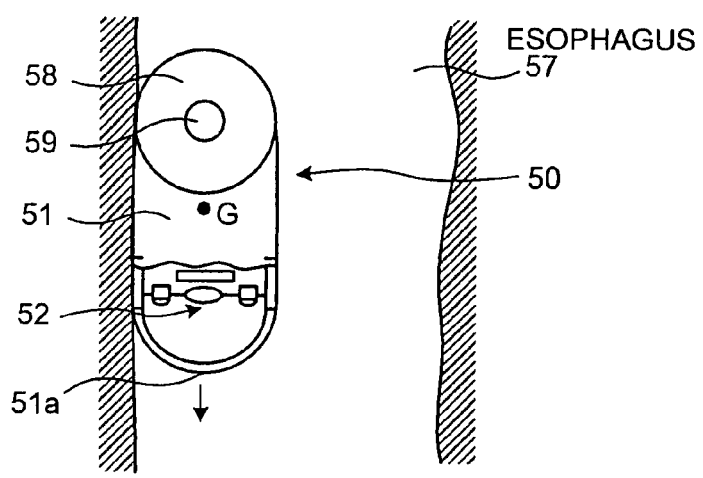

The case will be described, in which images of the cardiac portion of the stomach passing behind the esophagus are obtained upwardly for the observation. FIGS. 14A to 14C are explanatory views schematically showing progress of the capsule endoscope 50 of the third modified example within the esophagus 57. In this case, even when the capsule endoscope 50 is swallowed with the imaging direction reversed (upward) as shown in FIG. 14A, while it is falling down within the esophagus 57 of the subject 1, the pair of larger wheel members 58 protruding from the side surface of the capsule casing 51 comes into contact with the inner wall of the tube of the esophagus 57 and generates the friction, so that the capsule casing 51 may rotate around the rotary shafts 59. Further, the center of gravity G of the capsule casing 51 is positioned at the upper position than the pair of wheel members 58 (rotary shafts 59). As a consequence, the capsule endoscope 50 becomes unstable, and the capsule casing 51 rotates around the rotary shafts 59 upside down such that the center of gravity G may be positioned at the lower position than the wheel members 58 (rotary shafts 59), as shown in FIGS. 14B and 14C. Accordingly, the front cover 51a is headed downward and it is possible to obtain images with the forwarding direction (downward) of the capsule endoscope 50 fixed as the desired imaging direction.

For example, as shown in FIG. 14C, when the capsule endoscope 50 is swallowed in the desired imaging direction, the capsule casing 51 does not rotate upside down owing to the positional relationship between the center of gravity G and the pair of wheel members 58.

In the fourth embodiment and the third modified example, the forwarding direction (downward) of the capsule endoscope 50 is fixed as the desired imaging direction, and the pair of convex members 53 and the pair of wheel members 58 are positioned at the rear side away from the center of gravity G. However, when the tailing direction of the capsule endoscope 50 (upward) is fixed as the desired imaging direction, the pair of convex members 53 and the pair of wheel members 58 may be arranged in the front side (in the side of the front cover 51a) away from the center of gravity G.

Figure 15:
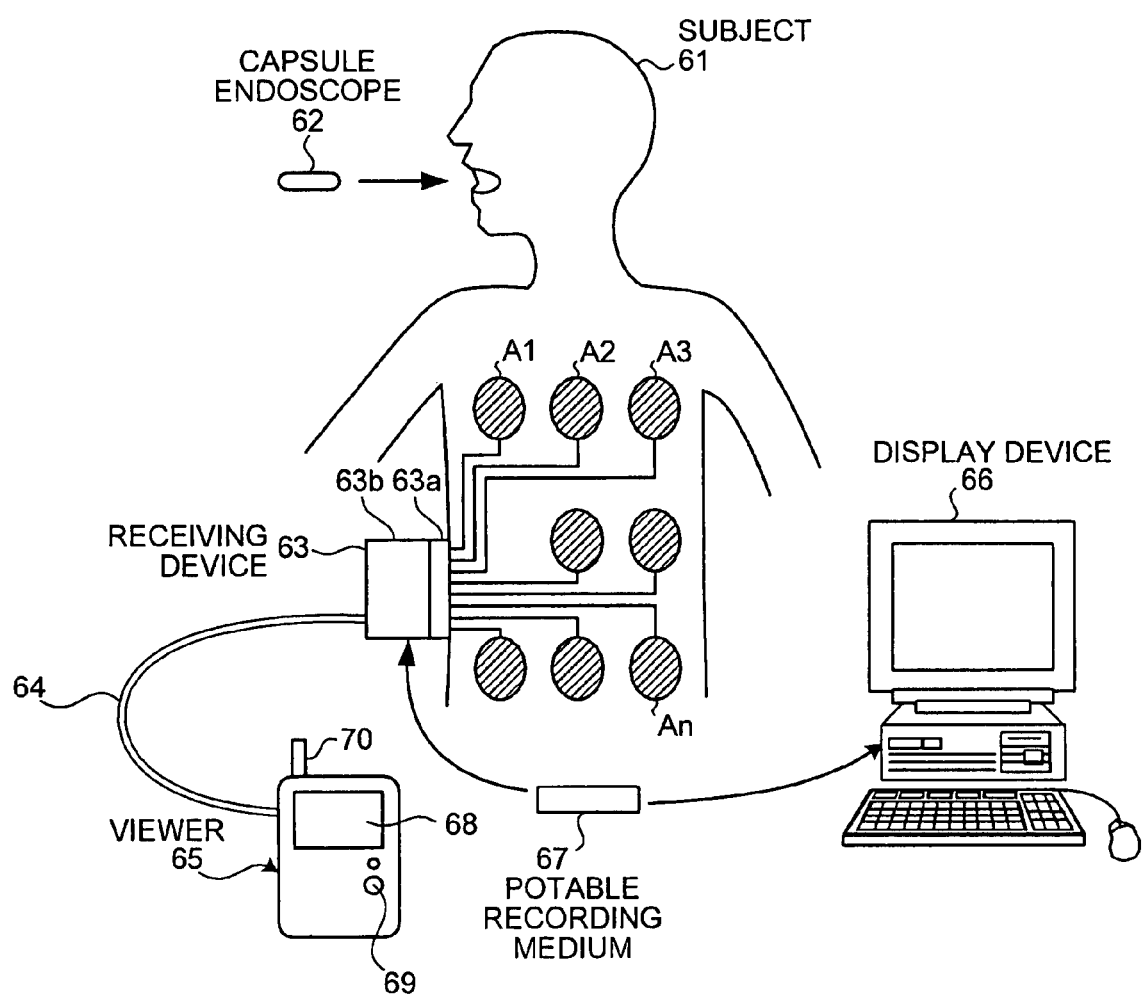
FIG. 15 is a schematic diagram showing the whole structure of a radio in-vivo information acquiring system that is a preferred embodiment of an in-vivo image capturing system according to the invention.

FIG. 15 is a schematic diagram showing an entire configuration of a radio in-vivo information acquiring system that is a preferred embodiment of the in-vivo image capturing system according to the invention. The in-vivo information acquiring system uses a monocular capsule endoscope which can obtain images only in one end direction as an example of the in-vivo image capturing apparatus. In the fifth embodiment, the forwarding direction of the capsule endoscope is fixed as the desired imaging direction. In FIG. 15, the in-vivo information acquiring system comprises a capsule endoscope 62, a receiving device 63, and a viewer 65. The capsule endoscope 62 is inserted into a subject 61 in order to obtain images inside the body cavity and transmit data such as image signals. The receiving device 63 is used being carried with the subject 1 to receive radio signals transmitted from the capsule endoscope 62 inserted into the subject 61. The viewer 65 is wire-connected to the receiving device 63 through a viewer cable 64 in a removable way to briefly display the images obtained by the capsule endoscope 62 according to electric signals supplied from the receiving device 63.

The in-vivo information acquiring system according to the fifth embodiment further comprises a display device 66 which displays the images inside the body cavity based on the image signals received by the receiving device 63, and a portable recording medium 67 which transfers data between the receiving device 63 and the display device 66. The receiving device 63 has an antenna unit 63*a* including a plurality of receiving antennas A1 to An to be attached to the external surface of the subject 61, and a main receiving unit 63*b* which processes radio signals received through the antenna unit 63*a*. The units 63*a* and 63*b* are removably connected together through a connector. The receiving antennas A1 to An may be attached to, for example, a receiving jacket which the subject 61 may wear, and the subject 61 may be provided with the receiving antennas A1 to An through wearing the receiving jacket. In this case, the receiving antennas A1 to An are attachable to and detachable from the jacket.

The display device 66 is to display the images inside the body cavity obtained by the capsule endoscope 62, and it is formed in a workstation which displays the images based on data obtained by the portable recording medium 67. Specifically, the display device 66 may be formed to display the images directly like a CRT display and a liquid crystal display, and may be formed to output the images to another medium like a printer.

A CompactFlash® memory is used as the portable recording medium 67, it is attachable to and detachable from the receiving device 63 and the display device 66, and it may output or record information when it is inserted to the both. In the fifth embodiment, for example, before an examination, the portable recording medium 67 is inserted to the display device 66 of the workstation to store identification information such as an examination ID therein. Just before the examination, the portable recording medium 67 is inserted to the receiving device 63, and the receiving device 63 reads the identification information and registers it therein. While the capsule endoscope 62 is moving within the body cavity of the subject 61, the portable recording medium 67 is inserted to the receiving device 63 attached to the subject 61 and records the data transmitted from the capsule endoscope 62. After the capsule endoscope 62 is excreted from the subject 61, in other words, after the imaging inside the subject 61 is completed, the portable recording medium 67 is taken out from the receiving device 63 and inserted to the display device 66, so that the data recorded in the portable recording medium 67 is read out by the display device 66. Transfer of the data between the receiving device 63 and the display device 66 is carried out by the portable recording medium 67, thereby enabling the subject 61 to move freely during the imaging of the inside of the body cavity and contributing to shorten the time of data transfer between the receiving device 63 and the display device 66. Another recording device built in the receiving device 63, for example, a hard disk may be used in order to transfer the data between the receiving device 63 and the display device 66, with the both connected with or without wire.

The viewer 65 is formed in a portable size such that an operator may grip by the hand, provided with a function for displaying the images inside the body cavity based on the electric signals (image data inside the body cavity) supplied from the receiving device 63. In order to realize the function, the viewer 65 includes a display unit 68 formed by a compact LCD for image display. Reference numeral 69 is a power switch. The viewer 65 has a rod antenna 70 for realizing a receiving function for directly receiving the radio signals (image data inside the body cavity) transmitted from the capsule endoscope 62 without passing through the receiving device 63. Here, the viewer 65 and the capsule endoscope 62 configure an in-vivo image capturing system 71. In FIG. 15, though the receiving device 63 and the viewer 65 are connected together through a viewer cable 64, they are not always used connected together. When the real-time observation is not performed according to the received image of the receiving device 63, the viewer cable 64 is removed and the subject 61 carries only the receiving device 63.

Figure 16:
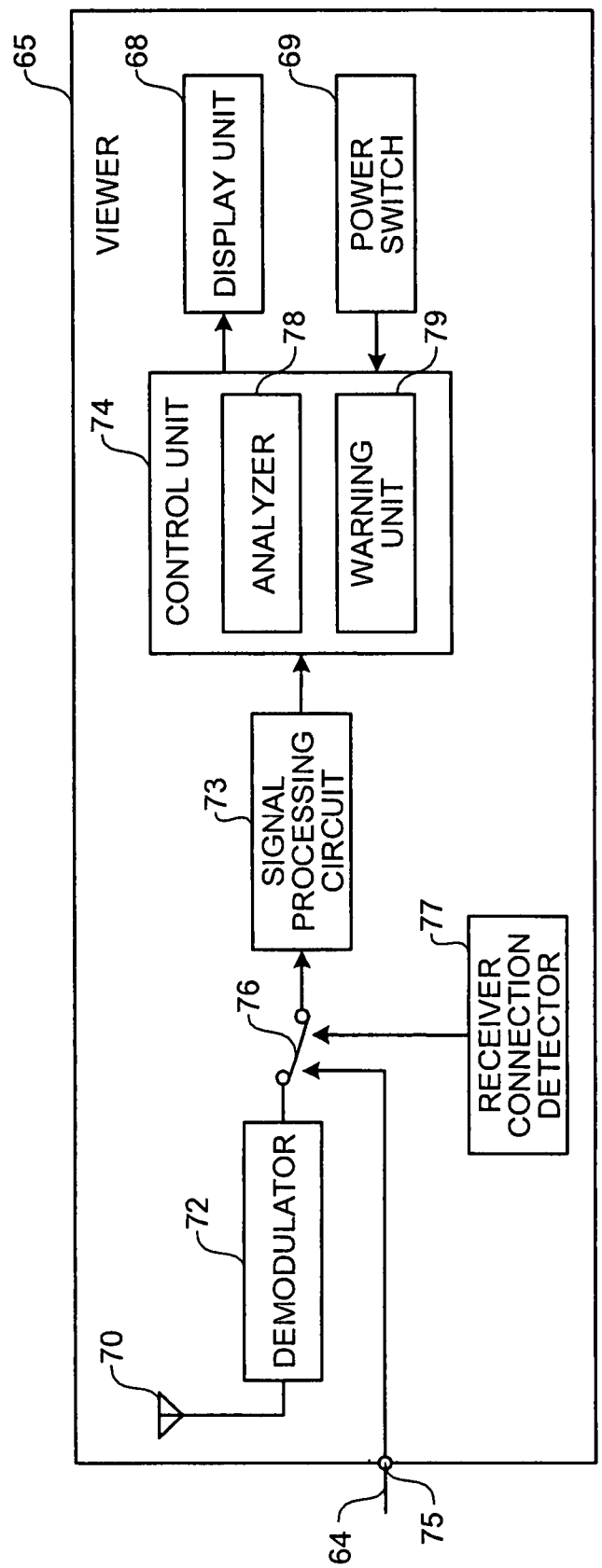
FIG. 16 is a schematic block diagram showing an internal circuit structure of a viewer.

Now, an internal circuit configuration of the viewer 65 will be descried. FIG. 16 is a schematic block diagram showing the internal circuit configuration of the viewer 65. The viewer 65 includes a demodulator 72 which demodulates the radio signals received through the antenna 70 and a signal processing circuit 73 which performs a predetermined signal processing on the demodulated electric signals. In addition to the signal processing circuit 73, the power switch 69 and the display unit 68 etc. are connected to a control unit 74 of a microcomputer configuration which has a CPU for controlling the entire operation of the viewer 65. The viewer 65 further includes a changeover switch 76 for switching the connection with the signal processing circuit 73 between the output side of the demodulator 72 and the side of the cable connector 75 to which the viewer cable 64 is connected, and a receiver connection detector 77 for controlling the changeover switch 76. Further, the viewer 65 includes a battery for operating each unit, although not illustrated.

The control unit 74 includes an analyzer 78 and a warning unit 79. The analyzer 78 is to determine whether the imaging direction of the capsule endoscope 62 is heading for the throat side or teeth side by analyzing image components obtained by an imaging optical system (not illustrated) of the capsule endoscope 62 inserted into the oral cavity of the subject 61 and staying there. More specifically, when the imaging direction of the capsule endoscope 62 staying in the oral cavity is heading for the teeth side, white-tinged image components are obtained. On the other hand, when the imaging direction is heading for the throat side, red-tinged or deep red components are obtained. Thus, the image components of the both portions are different. For this reason, when such a positive analytical result is obtained that the image components obtained by the imaging optical system include not less than a predetermined amount of white image components, it is determined that the capsule endoscope 62 is heading for the teeth side.

The warning unit 79 is to issue a warning to a user about the direction of the capsule endoscope 62 based on the analytical result of the analyzer 78. Specifically, when the positive analytical result is obtained by the analyzer 78, in other words, when the result that the capsule endoscope 62 is heading for the teeth side not for the throat side is obtained, the imaging direction is in the trailing direction and not the desired imaging direction (forward direction). Therefore, the warning unit 79 has a function of displaying a warning message such as "The direction of the capsule is reverse. Turn the swallowing direction." on the display unit 68.

Figure 17:
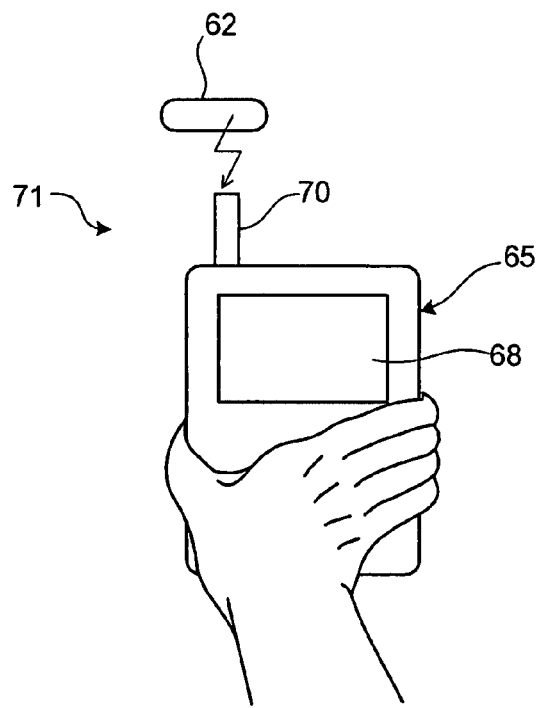
FIG. 17 is a front view showing the state of observing an obtained image of a capsule endoscope before it is swallowed.

Next, the processing at the start of the examination will be described. First, before the capsule endoscope 62 is swallowed, a doctor or a nurse, as shown in FIG. 17, holds the viewer 65 itself and makes it closer to the capsule endoscope 62 after turning on the power switch, to directly receive the radio signals from the capsule endoscope 62 through the antenna 70 and to display the obtained images on the display unit 68. Then, the imaging direction of the capsule endoscope 62 may be confirmed, so that the swallowing direction of the capsule endoscope 62 can be directed to the subject 61.

Figure 18:
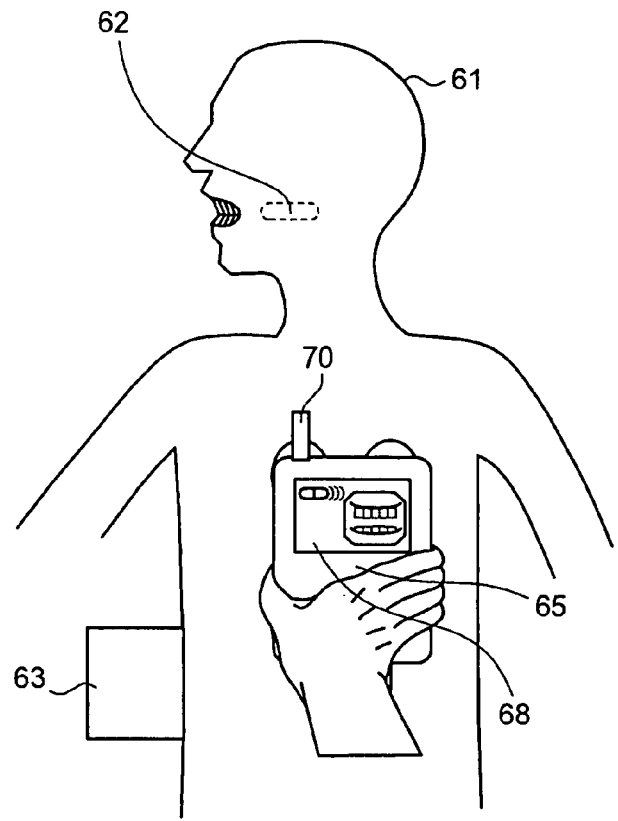
FIG. 18 is a front view showing the state of detecting a direction when the capsule endoscope exists within an oral cavity.

After the capsule endoscope 62 is put into the oral cavity, a doctor or a nurse, as shown in FIG. 18, holds the viewer 65 itself and makes it closer to the capsule endoscope 62 within the oral cavity of the subject 61, to directly receive the radio signals from the capsule endoscope 62 through the antenna 70, and then the image data inside the oral cavity is obtained directly. The analyzer 78 analyzes image components of the image data inside the oral cavity, hence to determine the direction of the capsule endoscope 62 within the oral cavity. When such a positive analytical result is obtained that the image components obtained by the imaging optical system include not less than a predetermined amount of white image components, the capsule endoscope 62 is determined to be heading for the teeth side. In this case, because the imaging direction is in the trailing side and not the desired imaging direction (forward direction), the warning unit 79 causes the display unit 68 to display a warning message such as "The direction of the capsule is reverse. Turn the swallowing direction." Accordingly, a doctor or a nurse directs the subject 61 to turn the capsule endoscope 62 in the oral cavity and then to swallow it. Therefore, it is possible to obtain images in the desired direction with its imaging direction fixed forward. On the other hand, when the negative analytical result that the image components obtained by the imaging optical system include less than the predetermined amount of white image components is obtained, the capsule endoscope 62 is determined to be heading for the throat side and no warning is issued.

As mentioned above, according to the fifth embodiment, paying attention to the difference of the image components between the throat side and the teeth side in the oral cavity, the image components inside the oral cavity are analyzed, which are obtained by the monocular capsule endoscope 62 (capsule casing) capable of obtaining images only in one direction, and according to the analytical result, a warning about the direction of the capsule endoscope 62 (capsule casing) is issued to a user when the swallowing direction in the oral cavity is not the desired imaging direction. According to the warning, the user turns the swallowing direction of the capsule endoscope 62. This makes it possible to obtain images in the desired direction in the monocular type.

The analyzer 78 according to the fifth embodiment determines the direction of the capsule endoscope 62 according to whether the white image in the oral cavity is not less than the predetermined amount or not. However, it is possible to determine it according to whether the brightness of the image components is not less than a predetermined value or not because the images obtained in the teeth side include image data of higher brightness caused by glittering of the teeth. In order to improve the accuracy of the analysis and determination, both conditions of the white image components and the brightness may be adopted. In the fifth embodiment, although the analyzer 78 is provided in the viewer 65 to analyze the image components, it is possible to analyze them in the internal processing within the capsule endoscope 62 and transmit the analytical result to the viewer 65.

In the fifth embodiment, the forwarding direction of the capsule endoscope 62 is fixed as the desired imaging direction, and the case in which the capsule endoscope 62 is heading for the teeth side in the oral cavity is targeted for a warning. However, when the trailing direction of the capsule endoscope 62 is fixed as the desired imaging direction, a warning may be issued when the capsule endoscope 62 is determined to be heading for the throat side.

Figure 19:
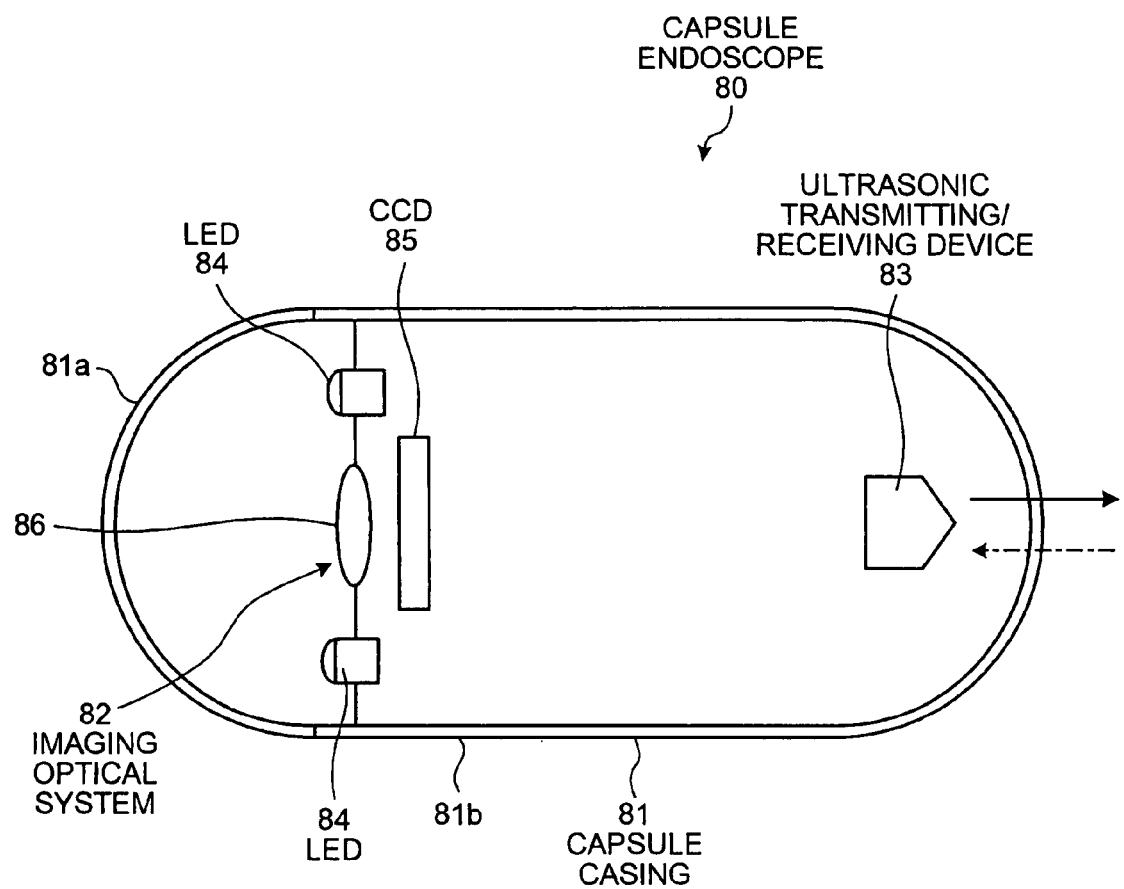
FIG. 19 is a longitudinal section view showing a schematic structure of a capsule endoscope for use in an in-vivo image capturing system according to a sixth embodiment of the invention.

FIG. 19 is a longitudinal sectional view showing a schematic configuration of a capsule endoscope for use in an in-vivo image capturing system according to a sixth embodiment of the invention. A capsule endoscope 80 according to the sixth embodiment is used in the in-vivo information acquiring system comprising the viewer 65 as shown in FIG. 15, instead of the capsule endoscope 62.

The capsule endoscope 80 according to the sixth embodiment is formed as the monocular type, comprising a capsule casing 81 which may be inserted into the body cavity of the subject 61 and an imaging optical system 82, built in the capsule casing 81, which can obtain images only in one direction. The capsule endoscope 80 is further includes an ultrasonic transmitting/receiving device 83 arranged in the rear end portion (the end portion opposite to the imaging optical system 82) of the capsule casing 81, in addition to a battery, circuit components, and an antenna which are not illustrated.

The capsule casing 81 is of a size swallowable from the oral cavity into the body of the subject 61. The capsule casing 81 is formed into an outer case which is sealed off a liquid by elastically fitting a substantially hemispheric, transparent or translucent front cover 81*a* to a cup-shaped body cover 81*b* made of a colored material which does not allow the visible light to pass through.

The imaging optical system 82 within the capsule casing 81 includes a plurality of light emitting elements 84 (hereinafter, referred to as "LED 84") which emit illumination light for illuminating a portion of the subject within the body cavity through the front cover 81*a*, an imaging device 85 (hereinafter, referred to as "CCD 85") such as CCD or CMOS which, upon receipt of the reflected light of the illumination light, images the portion of the subject, and an image forming lens 86 which forms an image of a target on the CCD 85. The imaging optical system 82 can obtain images only in the direction of one end at the side of the front cover 81*a*. The ultrasonic transmitting/receiving device 83 is to emit ultrasonic backward at the rear end of the capsule endoscope 81 and to receive the reflected and returned ultrasonic.

Figure 20:
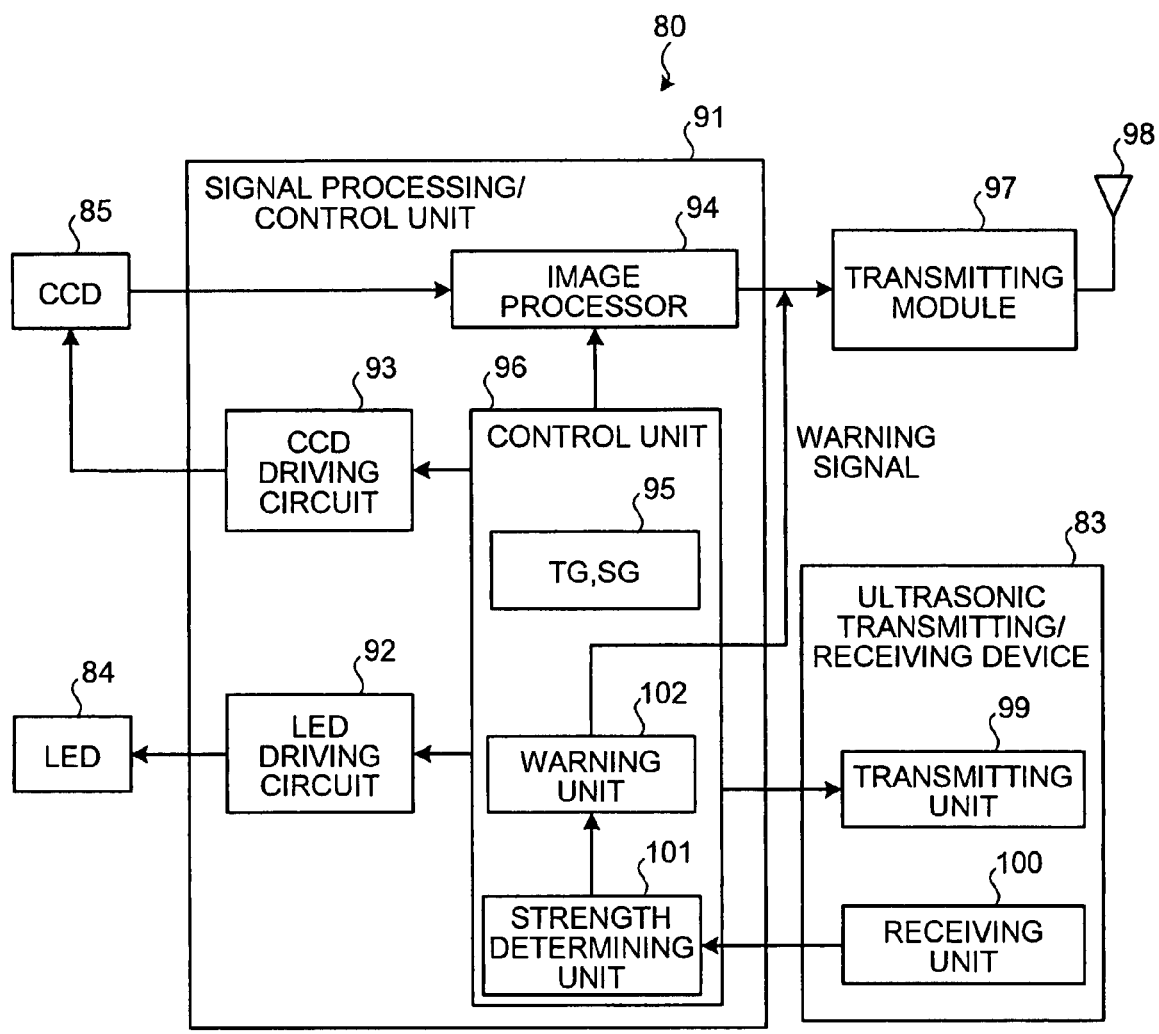
FIG. 20 is a schematic block diagram showing the internal circuit structure of the capsule endoscope.

Next, an internal circuit configuration of the capsule endoscope 80 will be described with reference to FIG. 20. FIG. 20 is a schematic block diagram showing the internal circuit configuration of the capsule endoscope 80. A signal processing/control unit 91 is to control the LED 84 and the CCD 85, and it has an LED driving circuit 92 and a CCD driving circuit 93 corresponding to the LED 84 and the CCD 85, respectively. The signal processing/control unit 91 has an image processor 94 which performs predetermined imaging processing including a correlated double sampling processing, amplification processing, A/D converting processing, and multiplexing processing on output signals supplied from the CCD 85. The signal processing/control unit 91 further includes a control unit 96 which has a timing generator (TG) and a sync generator (SG) 95 for generating various timing signals and synchronization signals. The signal processing/control unit 91 controls the operation and the operation timing of the driving circuits 92 and 93 and the image processor 94 based on the timing signals and the synchronization signals generated by the timing generator and the sync generator 95.

The capsule endoscope 80 includes a transmitting module 97 and a transmitting antenna 98 which are provided on an output path of imaging data obtained through the image processor 94 to output RF modulation signals. The control unit 96 is connected to the ultrasonic transmitting/receiving device 83 having a transmitting unit 99 for emitting ultrasonic and a receiving unit 100 for receiving the ultrasonic, to thereby control the operation timing for emitting the ultrasonic. The control unit 96 further includes a strength determining unit 101 and a warning unit 102. The strength determining unit 101 is to determine whether the received strength of the ultrasonic emitted by the transmitting unit 99 and received by the receiving unit 100 when the capsule endoscope 80 stays in the oral cavity is not less than a predetermined value or not. More specifically, when the ultrasonic is emitted in the oral cavity, the ultrasonic transmitting/receiving device 83 can be determined to be heading for the teeth side when the received strength of the ultrasonic received by the receiving unit 100 is not less than the predetermined value, because the teeth side is harder than the throat side and its reflected strength of the ultrasonic is stronger. In this case, the imaging direction (front cover 81) heads for the throat side.

The warning unit 102 is to issue a warning to a user about the direction of the capsule endoscope 80 based on the determined result of the strength determining unit 101. When the determining unit 101 obtains a negative analytical result, in other words, when it determines that the capsule endoscope 80 is heading for the teeth side not for the throat side, the imaging direction is in the trailing side and not the desired imaging direction (forward direction). Therefore, the warning unit 102 has a function of, by outputting a warning signal to the transmitting module 97 and transmitting the warning signal to the viewer 65 (refer to FIG. 15), displaying a warning message such as "The direction of the capsule is reverse. Turn the swallowing direction." on the display unit 68.

Now, the processing at the time of swallowing the capsule endoscope 80 will be described. While the capsule endoscope 80 is put into the oral cavity, the control unit 96 controls the transmitting unit 99 of the ultrasonic transmitting/receiving device 83 to transmit and output the ultrasonic. Thus, the capsule endoscope 80 emits the ultrasonic backward within the oral cavity. The ultrasonic reflected in the oral cavity is received by the receiving unit 100, and the receiving signal is output to the strength determining unit 101. The strength determining unit 101 determines the direction of the capsule endoscope 80 within the oral cavity by determining whether the received strength of the ultrasonic is more than a predetermined value or not. When such a negative result is obtained that the ultrasonic is emitted to the throat side and that the received strength of the ultrasonic is less than the predetermined value, the capsule endoscope 80 is determined to be heading for the teeth side. In this case, because the imaging direction is in the trailing side and not the desired imaging direction (forward direction), the warning unit 101 transmits and outputs the warning signal to the viewer 65, to for example, cause the display unit 68 to display a warning message such as "The direction of the capsule is reverse. Turn the swallowing direction.". Thereby, a doctor or a nurse directs the subject 61 to turn the direction of the capsule endoscope 80 in the oral cavity, and then, to swallow it. This makes it possible to obtain images in the desired direction with the imaging direction fixed forward. On the other hand, when the unit 101 obtains a positive result that the received strength of the ultrasonic is the predetermined value or more, the capsule endoscope 80 is determined to be heading for the throat side and no warning is issued.

As mentioned above, according to the sixth embodiment, paying attention to a difference in the hardness and the intensity of the reflected ultrasonic between the throat side and the teeth side within the oral cavity, the received strength of the ultrasonic emitted backward and reflected therefrom is determined, in the monocular capsule endoscope 80 (capsule casing 81) which can obtain images only in one direction within the oral cavity. In addition, a warning about the direction of the capsule endoscope 80 (capsule casing 81) is issued to a user according to the determined result. Consequently, when the swallowing direction is not the desired imaging direction, the user may turn the swallowing direction of the capsule endoscope 80, receiving the warning. Therefore, it is possible to obtain images in the desired direction in the monocular type.

In the sixth embodiment, although the strength determining unit 101 and the warning unit 102 are provided in the capsule endoscope 80 in order to determine the direction and make a warning, the received strength signal of the ultrasonic may be transmitted to the side of the viewer in order to do the same in the viewer side.

In the sixth embodiment, the forwarding direction of the capsule endoscope 80 is fixed as the desired imaging direction, and the case in which the capsule endoscope 80 heads for the teeth side within the oral cavity is targeted for a warning. However, when the tailing direction of the capsule endoscope 80 is fixed as the desired imaging direction, a warning may be issued when the capsule endoscope 80 is determined to be heading for the throat side.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An in-vivo image capturing system comprising:
    a capsule casing insertable into a subject from an oral cavity, the capsule casing including an imaging optical system capable of capturing images only in one end direction;
    an analyzing unit which determines whether an imaging direction of the capsule casing is heading for the throat side or teeth side of the subject by analyzing image components captured by the imaging optical system within the oral cavity; and
    a warning unit which issues a warning to a user about a direction of the capsule casing based on the determination by the analyzing unit.

2. The in-vivo image capturing system according to claim 1, wherein the analyzing unit checks whether the image components obtained by the imaging optical system include more than a predetermined amount of white image components.

3. The in-vivo image capturing system according to claim 2, wherein the warning unit issues a warning when the analyzing unit is determines that the imaging direction of the capsule casing is heading for the teeth side of the subject.

4. The in-vivo image capturing system according to claim 1, wherein the analyzing unit checks whether the image components captured by the imaging optical system include more than a predetermined amount of brightness.

5. The in-vivo image capturing system according to claim 4, wherein the warning unit issues a warning when the analytical result by the analyzing unit is positive.

6. The in-vivo image capturing system according to claim 1, wherein the analyzing unit and the warning unit are included in the capsule casing.

7. The in-vivo image capturing system according to claim 1, wherein the analyzing unit is provided inside the capsule casing and the warning unit is provided outside the capsule casing.

8. The in-vivo image capturing system according to claim 1, wherein the analyzing unit checks whether the image components obtained by the imaging optical system include more than a predetermined amount of red image components.

9. The in-vivo image capturing system according to claim 1, wherein the analyzing unit checks whether the image components obtained by the imaging optical system include more than a predetermined amount of white image components and more than a predetermined amount of brightness.

10. The in-vivo image capturing system according to claim 1, wherein the warning unit displays a message as the warning.

* * * * *